(12) United States Patent
Fan et al.

(10) Patent No.: US 10,466,243 B2
(45) Date of Patent: Nov. 5, 2019

(54) ANTIBODY AND APTAMER ENSEMBLE FOR CELL ISOLATION AND ENRICHMENT

(71) Applicant: UNIVERSITY OF FLORIDA RESEARCH FOUNDATION, INCORPORATED, Gainesville, FL (US)

(72) Inventors: Zhonghui Hugh Fan, Gainesville, FL (US); Jinling Zhang, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 502 days.

(21) Appl. No.: 15/035,518

(22) PCT Filed: Nov. 20, 2014

(86) PCT No.: PCT/US2014/066590
§ 371 (c)(1),
(2) Date: May 10, 2016

(87) PCT Pub. No.: WO2015/077441
PCT Pub. Date: May 28, 2015

(65) Prior Publication Data
US 2016/0291023 A1 Oct. 6, 2016

Related U.S. Application Data

(60) Provisional application No. 61/906,526, filed on Nov. 20, 2013.

(51) Int. Cl.
*G01N 33/543* (2006.01)
*G01N 33/574* (2006.01)
*B01L 3/00* (2006.01)

(52) U.S. Cl.
CPC .. *G01N 33/57426* (2013.01); *B01L 3/502753* (2013.01); *G01N 33/54366* (2013.01);
(Continued)

(58) Field of Classification Search
None
See application file for complete search history.

(56) References Cited

U.S. PATENT DOCUMENTS 5,646,001 A    7/1997  Terstappen
6,632,655 B1  10/2003  Mehta
(Continued)

FOREIGN PATENT DOCUMENTS

WO    WO 2013/044240    3/2013

OTHER PUBLICATIONS

Adams, A. A. et al. "Highly Efficient Circulating Tumor Cell Isolation from Whole Blood and Label-Free Enumeration Using Polymer-Based Microfluidics with an Integrated Conductivity Sensor" *Journal of the American Chemical Society*, Jun. 17, 2008, pp. 8633-8641, vol. 130.

(Continued)

*Primary Examiner* — Christopher L Chin
(74) *Attorney, Agent, or Firm* — Timothy H. Van Dyke; Beusse, Wolter, Sanks & Maire PLLC

(57) ABSTRACT

The subject invention pertains to devices and methods of isolating target cells from a population of cells. The devices comprise of microfluidic channels and aptamers and antibodies attached to the inner surface of the microfluidic channels, wherein the aptamers and the antibodies are capable of specific binding to one or more biomolecules present on the surface of the target cell. The methods of the current invention comprise passing the population of cells through the microfluidic channels to facilitate interaction and capture of the target cells by the aptamers and the (Continued)

antibodies attached to the inner surface of the microfluidic channels, washing to microfluidic channels by a washing solution to remove the cells non-specifically bound to the aptamers and the antibodies attached to the inner surface of the microfluidic channels, releasing the captured target cells from the microfluidic channels, and collecting the released target cells.

19 Claims, 10 Drawing Sheets

Specification includes a Sequence Listing.

(52) U.S. Cl.
CPC ... *B01L 2200/0668* (2013.01); *B01L 2300/12* (2013.01); *B01L 2300/16* (2013.01); *G01N 2333/91205* (2013.01)

(56) References Cited

U.S. PATENT DOCUMENTS

| | | | |
|---|---|---|---|
| 2003/0087265 | A1 | 5/2003 | Sauter |
| 2006/0147941 | A1 | 7/2006 | Su |
| 2008/0020368 | A1 | 1/2008 | Yang |
| 2010/0105053 | A1 | 4/2010 | Cho et al. |
| 2010/0123457 | A1 | 5/2010 | Shinoda |
| 2011/0070581 | A1 | 3/2011 | Gupta |
| 2011/0158901 | A1 | 6/2011 | Santra |
| 2012/0070833 | A1 | 3/2012 | Wang et al. |
| 2012/0077246 | A1 | 3/2012 | Hong et al. |
| 2012/0100521 | A1 | 4/2012 | Soper et al. |
| 2013/0035630 | A1 | 2/2013 | Chen |

OTHER PUBLICATIONS

Capretto, L. et al. "Micromixing Within Microfluidic Devices" *Topics in Current Chemistry*, Apr. 28, 2011, pp. 27-68, vol. 304.

Chen, W. et al. "Nanoroughened Surfaces for Efficient Capture of Circulating Tumor Cells without Using Capture Antibodies" *American Chemical Society Nano*, 2013, pp. 566-575, vol. 7, No. 1.

Dharmasiri, U. et al. "Microsystems for the Capture of Low-Abundance Cells" *Annual Review of Analytical Chemistry*, Apr. 1, 2010, pp. 409-431, vol. 3.

Dharmasiri, U. et al. "High-Throughput Selection, Enumeration, Electrokinetic Manipulation, and Molecular Profiling of Low-Abundance Circulating Tumor Cells Using a Microfluidic System" *Analytical Chemistry*, Feb. 14, 2011, pp. 2301-2309, vol. 83.

Gleghorn, J. P. et al. "Capture of circulating tumor cells from whole blood of prostate cancer patients using geometrically enhanced differential immunocapture (GEDI) and a prostate-specific antibody" *Lab on a Chip*, 2010, pp. 27-29, vol. 10.

Guo, J. et al. "Detecting Carcinoma Cells in Peripheral Blood of Patients With Hepatocellular Carcinoma by Immunomagnetic Beads and RT-PCR" *Journal of Clinical Gastroenterology*, Sep. 2007, pp. 783-788, vol. 41, No. 8.

Han, W. et al. "Nanoparticle Coatings for Enhanced Capture of Flowing Cells in Microtubes" *American Chemical Society Nano*, 2010, pp. 174-180, vol. 4, No. 1.

Helo, P. et al. "Circulating Prostate Tumor Cells Detected by Reverse Transcription-PCR in Men with Localized or Castration-Refractory Prostate Cancer: Concordance with CellSearch Assay and Association with Bone Metastases and with Survival" *Clinical Chemistry*, 2009, pp. 765-773, vol. 55, No. 4.

Hoshino, K. et al. "Microchip-based immunomagnetic detection of circulating tumor cells" *Lab on a Chip*, 2011, pp. 3449-3457, vol. 11.

Kotz, K. T. et al. "Clinical microfluidics for neutrophil genomics and proteomics" *Nature Medicine*, Sep. 2010, pp. 1042-1048, vol. 16, No. 9.

Maheswaran, S. et al. "Detection of Mutations in EGFR in Circulating Lung-Cancer Cells" *The New England Journal of Medicine*, Jul. 24, 2008, pp. 366-377, vol. 359, No. 4.

Mikolajczyk, S. D. et al. "Detection of EpCAM-Negative and Cytokeratin-Negative Circulating Tumor Cells in Peripheral Blood" *Journal of Oncology*, 2011, pp. 1-10, vol. 2011.

Myung, J. H. et al. "Dendrimer-Mediated Multivalent Binding for the Enhanced Capture of Tumor Cells" *Angewandte Chemie International Edition*, 2011, pp. 11769-11772, vol. 50.

Nagrath, S. et al. "Isolation of rare circulating tumour cells in cancer patients by microchip technology" *Nature*, Dec. 20-27, 2007, pp. 1235-1241, vol. 450.

O'Donoghue, M. B. et al. "Single-molecule atomic force microscopy on live cells compares aptamer and antibody rupture forces" *Analytical and Bioanalytical Chemistry*, 2012, pp. 3205-3209, vol. 402.

Pantel, K. et al. "Detection, clinical relevance and specific biological properties of disseminating tumour cells" *Nature Reviews Cancer*, May 2008, pp. 329-340, vol. 8.

Phillips, J. A. et al. "Enrichment of Cancer Cells Using Aptamers Immobilized on a Microfluidic Channel" *Analytical Chemistry*, Feb. 1, 2009, pp. 1033-1039, vol. 81, No. 3.

Riethdorf, S. et al. "Detection of Circulating Tumor Cells in Peripheral Blood of Patients with Metastatic Breast Cancer: A Validation Study of the CellSearch System" *Clinical Cancer Research*, Feb. 1, 2007, pp. 920-928, vol. 13, No. 3.

Saliba, A-E. et al. "Microfluidic sorting and multimodal typing of cancer cells in self-assembled magnetic arrays" *Proceedings of the National Academy of Sciences of the United States of America*, Aug. 17, 2010, pp. 14524-14529, vol. 107, No. 33.

Sheng, W. et al. "Aptamer-Enabled Efficient Isolation of Cancer Cells from Whole Blood Using a Microfluidic Device" *Analytical Chemistry*, Apr. 7, 2012, pp. 4199-4206, vol. 84.

Sheng, W. et al. "Multivalent DNA Nanospheres for Enhanced Capture of Cancer Cells in Microfluidic Devices" *American Chemical Society Nano*, 2013, pp. 7067-7076, vol. 7, No. 8.

Sheng, W. et al. "Capture, Release and Culture of Circulating Tumor Cells from Pancreatic Cancer Patients using an Enhanced Mixing Chip" *Lab on a Chip*, Jan. 7, 2014, pp. 1-20, vol. 14, No. 1.

Sia, S. K. et al. "Microfluidic devices fabricated in poly(dimethylsiloxane) for biological studies" *Electrophoresis*, 2003, pp. 3563-3576, vol. 24.

Stott, S. L. et al. "Isolation of circulating tumor cells using a microvortex-generating herringbone-chip" *Proceedings of the National Academy of Sciences of the United States of America*, Oct. 26, 2010, pp. 18392-18397, vol. 107, No. 43.

Wang, S. et al. "Nano "Fly Paper" Technology for the Capture of Circulating Tumor Cells" *Methods in Molecular Biology*, 2011, pp. 141-150, vol. 726, Cpt. 10.

Wang, S. et al. "Three-Dimensional Nanostructured Substrates toward Efficient Capture of Circulating Tumor Cells" *Angewandte Chemie International Edition*, 2009, pp. 8970-8973, vol. 48.

Wang, S. et al. "Highly Efficient Capture of Circulating Tumor Cells by Using Nanostructured Silicon Substrates with Integrated Chaotic Micromixers" *Angewandte Chemie International Edition*, 2011, pp. 3084-3088, vol. 50.

Xu, Y. et al. "Aptamer-Based Microfluidic Device for Enrichment, Sorting, and Detection of Multiple Cancer Cells" *Analytical Chemistry*, Sep. 1, 2009, pp. 7436-7442, vol. 81, No. 17.

Yamamura, S. et al. "Accurate Detection of Carcinoma Cells by Use of a Cell Microarray Chip" *PLoS One*, Mar. 2012, pp. 1-9, vol. 7, No. 3.

Zhao, M. et al. An Automated High-Throughput Counting Method for Screening Circulating Tumor Cells in Peripheral Blood *Analytical Chemistry*, Feb. 6, 2013, pp. 2465-2471, vol. 85.

Zheng, X. et al. "A high-performance microsystem for isolating circulating tumor cells" *Lab on a Chip*, 2011, pp. 3269-3276, vol. 11.

Written Opinion in International Application No. PCT/US2014/066590, Feb. 19, 2015, pp. 1-9.

(56) References Cited

OTHER PUBLICATIONS

Allard, W.J. et al., "Tumor Cells Circulate in the Peripheral Blood of All Major Carcinomas but not in Healthy Subjects or Patients With Nonmalignant Diseases," Clinical Cancer Research, Oct. 15, 2004, pp. 6897-6904, vol. 10.

Arya, S.K., et al., "Enrichment, detection and clinical significance of circulating tumor cells" Lab Chip, 2013, pp. 1995-2027, vol. 13.

Cen, P., et al., "Circulating tumor cells in the diagnosis and management of pancreatic cancer" Biochimica et Biophysica Acta, 2012, pp. 350-356, vol. 1826.

Chen, L., et al., "Aptamer-Mediated Efficient Capture and Release of T Lymphocytes on Nanostructured Surfaces" Advanced Materials, 2011, pp. 4376-4380, vol. 23.

Chen, J., et al., "Microfluidic approaches for cancer cell detection, characterization, and separation" Lab Chip, Feb. 15, 2012, pp. 1753-1767, vol. 12.

Forbes, T.P., et al., "Engineering and analysis of surface interactions in a microfluidic herringbone micromixer," Lab Chip, May 18, 2013, pp. 2634-2637, vol. 12.

He, W., et al., "In vivo quantitation of rare circulating tumor cells by multiphoton intravital flow cytometry," Proceedings of the National Academy of Sciences, Jul. 10, 2007, pp. 11760-11765, vol. 104, No. 28.

Huang, Y-F, et al., "Cancer Cell Targeting Using Multiple Aptamers Conjugated on Nanorods," Analytical Chemistry, Feb. 1, 2008, pp. 567-572, vol. 80, No. 3.

Issadore, D., et al., "Ultrasensitive clinical enumeration of rare cells ex vivo using a µ-Hall detector," Science Translational Medicine, Jul. 4, 2012, pp. 1-22, vol. 4, No. 141.

Jiao, Re, et al., "Cancer-Targeting Multifunctionalized Gold Nanoparticles in Imaging and Therapy," Current Medicinal Chemistry, 2011, pp. 2086-2102, vol. 18, No. 14.

Kang, J.H., et al., "A combined micromagnetic-microfluidic device for rapid capture and culture of rare circulating tumor cells," Lab Chip, Mar. 8, 2012, pp. 2175-2181, vol. 12.

Khoja, L, et al., "A pilot study to explore circulating tumour cells in pancreatic cancer as a novel biomarker," British Journal of Cancer, 2012, pp. 508-516, vol. 106.

Lee, S-K et al., "Nanowire Substrate-based Laser Scanning Cytometry for Quantitation of Circulating Tumor Cells," Nano Letters, Jun. 13, 2012, pp. 2697-2704, vol. 12, No. 6.

Lustberg, M., et al., "Emerging Technologies for CTC Detection Based on Depletion of Normal Cells," in Minimal Residual Disease and circulating Tumor Cells in Breast Cancer, Recent Results in Cancer Research, eds M. Ignatiadis et al., 2012, pp. 97-110, vol. 195.

Ozkumur, E., et al., Inertial Focusing for Tumor Antigen-Dependent and-Independent Sorting of Rare Circulating Tumor Cells, Science Translational Medicine, Apr. 3, 2013, pp. 1-20, vol. 5, No. 179.

Schiro, P.G., et al., "Sensitive and High-Throughput Isolation of Rare Cells from Peripheral Blood with Ensemble-Decision Aliquot Ranking," Angewandte Chemie International Edition England, May 7, 2012, pp. 4618-4622, vol. 51, No. 19.

Shangguan, D., et al., "Aptamers evolved from live cells as effective molecular probes for cancer study," Proceedings of the National Academy of Sciences, Aug. 8, 2006, pp. 11838-11843, vol. 103, No. 32.

Stroock, A.D., et al., "Chaotic Mixer for Microchannels," Science, Jan. 25, 2002, pp. 647-651, vol. 295.

Tang, Z., et al., "Selection of Aptamers for Molecular Recognition and Characterization of Cancer Cells," Analytical Chemistry, Jul. 1, 2007, pp. 4900-4907, vol. 79, No. 13.

Tjensvoll, K. et al., "Circulating tumor cells in pancreatic cancer patients: Methods of detection and clinical Implications," International Journal of Cancer, 2013, pp. 1-8, vol. 134.

Valencia, P.M., et al., "Microfluidic technologies for accelerating the clinical translation of nanoparticles," National Nanotechnology, Oct. 2012, pp. 623-629, vol. 7, No. 10.

Yu, M., et al., "Circulating tumor cells: approaches to isolation and characterization," The Journal of Cell Biology, 2011, pp. 373-382, vol. 192, No. 3.

Zhao, W., et al., "Bioinspired multivalent DNA network for capture and release of cells," Proceedings of the National Academy of Sciences, Nov. 27, 2012, pp. 19626-19631, vol. 109, No. 48.

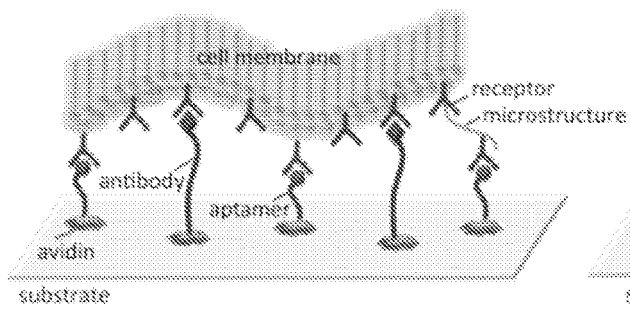
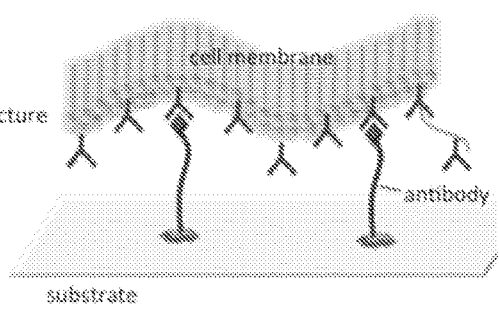
Figure 1A
Figure 1B
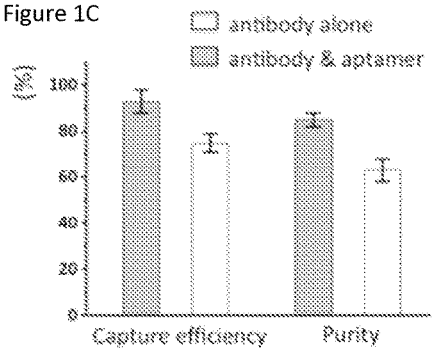
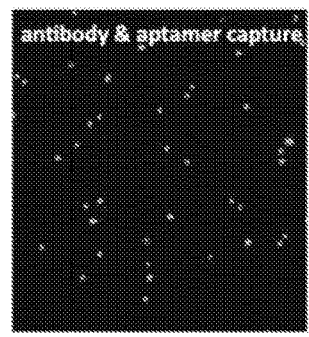
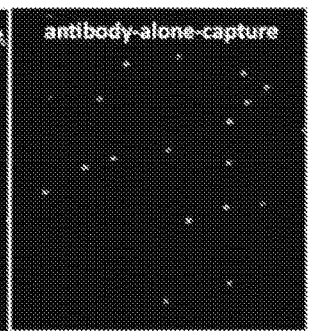
Figure 1C
Figure 1D
Figure 1E

ANTIBODY AND APTAMER ENSEMBLE FOR CELL ISOLATION AND ENRICHMENT

CROSS-REFERENCE TO RELATED APPLICATIONS

This application is in the U.S. national stage application of International Patent Application No. PCT/US2014/066590, filed Nov. 20, 2014, which claims the benefit of U.S. Provisional Application Ser. No. 61/906,526, filed Nov. 20, 2013, the disclosures of which are hereby incorporated by reference in their entirety, including all figures, tables and amino acid or nucleic acid sequences.

This invention was made with government support under K25CA149080 awarded by National Institutes of Health. The government has certain rights in the invention.

The Sequence Listing for this application is labeled "Seq-List.txt" which was created on Nov. 20, 2014 and is 6 KB. The entire contents of the sequence listing is incorporated herein by reference in its entirety.

BACKGROUND OF THE INVENTION

The enrichment and capture of target cells, for example, cancer cells, bacteria, viruses and other pathogens, from peripheral blood are of great importance for clinical disease diagnosis, therapy monitoring, biology study, and drug development.[1-3]

Circulating tumor cells (CTCs) are cancer cells spontaneously circulating in the peripheral blood or spreading iatrogenic into blood vessels, which is an early step in the cascade of events leading to metastasis.[4] Capture of CTCs provide a potentially accessible source for detection, characterization, and monitoring of cancers. However, isolation of these cells is a significant technological challenge due to their rare numbers and their low recovery rate following traditional batch purification techniques. There are a variety of conventional technologies, such as immuno-magnetic enrichment, flow cytometric cell sorting or polymerase chain reactions (PCR)-based methodology,[2, 5-8] but these are multistep technologies which are complex and have insufficient capture efficiency.

Recent microfluidic CTC devices using monovalent capture agents, including antibodies[9-11] and nucleic acid aptamers[12-13] represent a promising approach to capture cancer cells with highly efficient processing of complex cellular fluids,[14-15] greater simplicity, sensitivity[16-17] and throughput.[10, 18-19] However, monovalent adhesion ligands have difficulties in capturing large-sized entities, such as cells under high shear stress; a flow rate with low shear stress will render the assay time-consuming to process large volumes of blood samples. Thus, most of those devices for CTC capture are designed with complex channel topologies including microposts,[9] herringbone grooves,[20] or 3D structures.[21] Even with these geometries, efficient cell separation requires low shear stress conditions to maximize cell-surface contact.[22]

The cell surface has certain structures that cause higher contact chances than a flat surface,[23] as evidenced from enhanced local topographic interactions between the rough substrates and nanoscale cellular surface components.[24] Both aptamer and antibody have strong non-covalent interactions with cell surface binding sites, for example, cell surface receptors and other biomolecules. However, aptamers are much smaller with molecular weights of about 8-15 kDa, compared to antibodies with molecular weights of 150 kDa.[25] Due to the shape of a cell and a surface structure coated with nanoscale microvilli and filopodia,[26] the combination of aptamers and antibodies with different molecular size can increase the accessibility of biomolecules on the surface of cells and facilitate interactions between cell surface biomolecules and capture agents. This would permit cell capture under high flow rates. Therefore, a combination of aptamers and antibodies can provide for the capture of target cells by binding to cell surface binding sites in a cooperative manner, leading to higher cell capture efficiency (FIGS. 1a and 1b) and solve the need for efficient target cell (e.g., CTC) capture at high flow rate and high shear stress.

BRIEF SUMMARY OF THE INVENTION

The current invention provides microfluidic devices to capture and isolate target cells from a population of cells using aptamers and antibodies capable of specific binding to biomolecules present on the surface of the target cells. The microfluidic devices of the current invention comprise:
 a) one or more microfluidic channels, and
 b) one or more aptamers and one or more antibodies attached to the inner surface of said one or more microfluidic channels,
wherein said one or more aptamers and said one or more antibodies are capable of specifically binding to one or more biomolecules present on the surface of the target cell.

Methods for isolating a target cell from a population of cells are also provided, the methods comprising passing the population of cells through the microfluidic devices to facilitate interaction and capture of the target cell by said one or more aptamers and said one or more antibodies attached to the inner surface of the microfluidic channels, washing the microfluidic devices to remove cells non-specifically bound said one or more aptamers and said one or more antibodies within the microfluidic channels of the device, releasing the captured target cell bound to the one or more aptamers and said one or more antibodies, and collecting the released target cell.

BRIEF DESCRIPTION OF THE DRAWINGS

FIGS. 1A-1E. (a) With a combination of antibodies and aptamers multiple receptors on the cell membrane can bind strongly to the substrate in cooperative multivalent interactions. (b) With antibodies alone, target cells bind to substrates via fewer monovalent interactions. (c) Comparison of capture efficiency and cell purity between the combination of aptamers and antibodies with the antibody alone. (Flow rate of 1.2 µL/s.) (d, e) Representative image of the target CEM cells (green) and Ramos cells (red) captured in the device using (d) antibody and aptamer combination or (e) anti-PTK7 antibody alone.

FIGS. 5A and 5B. (a) Representative image of captured CEM cells (DiI+, DAPI+) from whole blood; the DAPI+ cells (blue only) are non-specifically captured white blood cells. (b) Calibration plot of cancer cell capture from whole blood and buffer solution with different cell concentrations at 2.0 μL/s; solid lines represent linear fitting. Error bars represent standard deviations (n=3).

(FIG. 9A) CEM cells selectively bind with sgc8 aptamers. (Fig. B) Ramos cells selectively bind with TD05 aptamers (Anal. Chem. 2012, 84:4199-4206).

FIG. 10A) and Ramos cells captured with anti-PTK7 and TD05 (green; FIG. 10B).

FIG. 11A) and Ramos cells captured with sgc8 and anti-EpCAM (green; FIG. 11B).

BRIEF DESCRIPTION OF THE SEQUENCES

Figure 2:
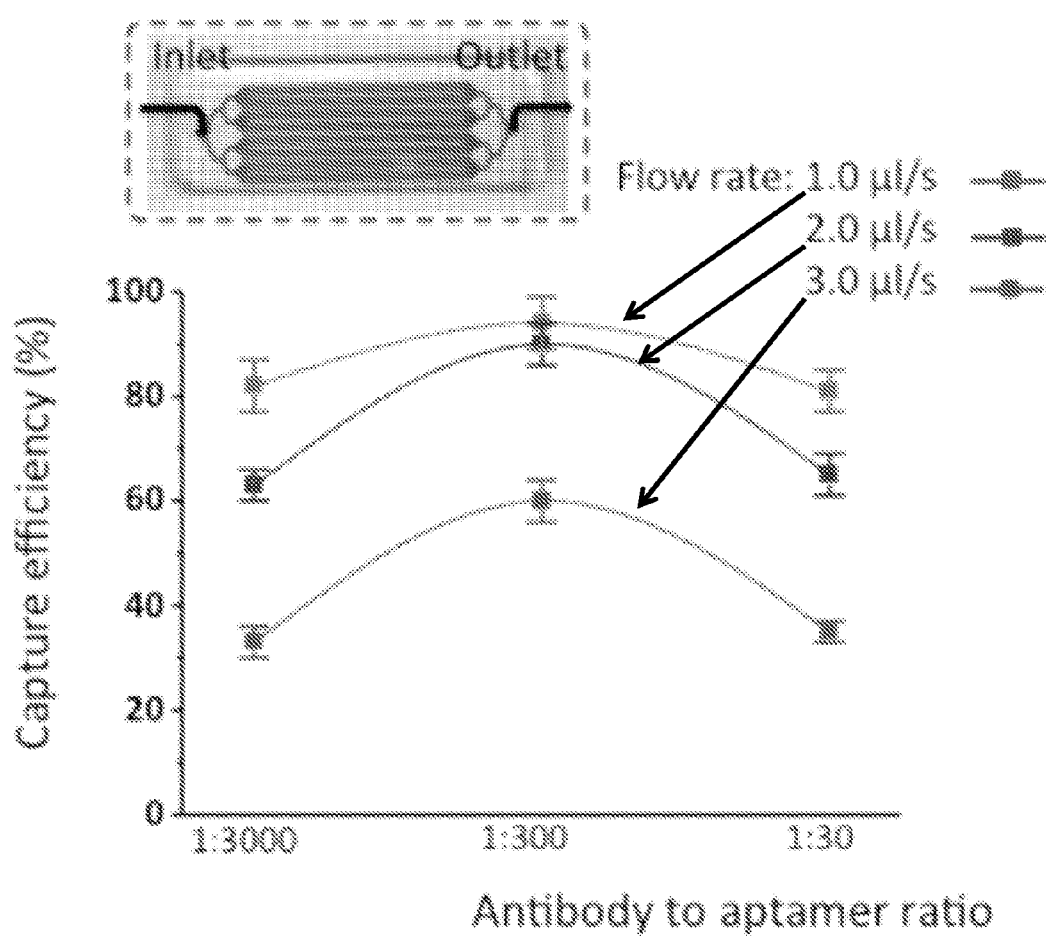
FIG. 2. Optimization of the ratio of antibodies to aptamers at a flow rate ranging from 1.0 µL/s to 3.0 µL/s. A layout of an example of a device of the current invention is provided.

| Aptamer | Sequence |
|---|---|
| Sgc8 | 5'-ATC TAA CTG CTG CGC CGC CGG GAA AAT ACT GTA CGG TTA GA-3' (SEQ ID NO: 1) |
| TD05 | 5'-AAC ACC GTG GAG GAT AGT TCG GTG GCT GTT CAG GGT CTC CTC CCG GTG-3' (SEQ ID NO: 2) |
| sgc3b | 5'-ACT TAT TCA ATT CCT GTG GGA AGG CTA TAG AGG GGC AGT CTA TGA ATA AG-3' (SEQ ID NO: 3) |
| Sgd5 | 5'-ATA CCA GCT TAT TCA ATT ATC GTG GGT CAC AGC AGC GGT TGT GAG GAA GAA AGG CGG ATA ACA GAT AAT AAG ATAGTAAGTGCAATCT-3' (SEQ ID NO: 4) |
| KH2B05 | 5'-ATC CAG AGT GAC GCA GCA CAC ACA ACC TGC TCAT AAA CTT TAC TCT GCT CGA ACC ATC TCT GGA CAC GGT GGC TTA GT-3' (SEQ ID NO: 5) |
| KH1A02 | 5'-ATC CAG AGT GAC GCA GCA GGC ATA GAT GTG CAG CTC CAA GGA GAA GAA GGA GTT CTG TGT ATT GGA CAC GGT GGC TTA GT-3' (SEQ ID NO: 6) |
| KH1C12 | 5'-ATC CAG AGT GAC GCA GCA TGC CCT AGT TAC TAC TAC TCT TTT TAG CAA ACG CCC TCG CTT TGG ACA CGG TGG CTT AGT-3' (SEQ ID NO: 7) |
| TLS11a | 5'-ACA GCA TCC CCA TGT GAA CAA TCG CAT TGT GAT TGT TAC GGT TTC CGC CTC ATG GAC GTG CTG-3' (SEQ ID NO: 8) |
| PP3 | 5'-ATC CAG AGT GAC GCA GCA CGA GCC AGA CAT CTC ACA CCT GTT GCA TAT ACA TTT TGC ATG GAC ACG GTG GCT TAG T-3' (SEQ ID NO: 9) |
| TV02 | 5'-ATC GTC TGC TCC GTC CAA TAC CTG CAT ATA CAC TTT GCA TGT GGT TTG GTG TGA GGT CGT GC-3' (SEQ ID NO: 10) |
| HCH07 | 5'-TAC CAG TGC GAT GCT CAG GCC GAT GTC AAC TTT TTC TAA CTC ACT GGT TTT GCC TGA CGC ATT CGG TTG AC-3' (SEQ ID NO: 11) |
| KDED2a-3 | 5'-TGC CCG CGA AAA CTG CTA TTA CGT GTG AGA GGA AAG ATC ACG CGG GTT CGT GGA CAC GG-3' (SEQ ID NO: 12) |
| KCHA10 | 5'-ATC CAG AGT GAC GCA GCA GGG GAG GCG AGA GCG CAC AAT AAC GAT GGT TGG GAC CCA ACT GTT TGG ACA CGG TGG CTT AGT-3' (SEQ ID NO: 13) |
| S11e | 5'-ATG CGA ACA GGT GGG TGG GTT GGG TGG ATT GTT CGG CTT CTT GAT-3' (SEQ ID NO: 14) |
| DOV4 | 5'-ACT CAA CGA ACG CTG TGG AGG GCA TCA GAT TAG GAT CTA TAG GTT CGG ACA TCG TGA GGA CCA GGA GAG CA-3' (SEQ ID NO: 15) |
| aptTOV1 | 5'-ATC CAG AGT GAC GCA GCA GAT CTG TGT AGG ATC GCA GTG TAG TGG ACA TTT GAT ACG ACT GGC TCG ACA CGG TGG CTT A-3' (SEQ ID NO: 16) |
| KMF2-1a | 5'-AGG CGG CAG TGT CAG AGT GAA TAG GGG ATG TAC AGG TCT GCA CCC ACT CGA GGA GTG ACT GAG CGA CGA AGA CCC C-3' (SEQ ID NO: 17) |
| EJ2 | 5'-AGT GGT CGA ACT ACA CAT CCT TGA ACT GCG AAA TTA TCT AC-3' (SEQ ID NO: 18) |
| CSC01 | 5'-ACC TTG GCT GTC GTG TTG TAG GTG GTT TGC TGC GGT GGG CTC AAG AAG AAA GCG CAA AGT CAG TGG TCA GAG CGT-3' (SEQ ID NO: 19) |
| Anti-EpCAM aptamer (SYL3C) | 5'-CAC TAC AGA GGT TGC GTC TGT CCC ACG TTG TCA TGG GGT GGC CTG-3' (SEQ ID NO: 20) |

-continued

| Aptamer | Sequence |
|---|---|
| Anti-EGFR aptamer | 5'-GGC GCU CCG ACC UUA GUC UCU GUG CCG CUA UAA UGC ACG GAU UUA AUC GCC GUA GAA AAG CAU GUC AAA GCC GGA ACC GUG UAG CAC AGC AGAGAAUUAAAUGCCCGCCAUG ACCAG-3' (SEQ ID NO: 21) |
| Anti-PSMA aptamer | 5'-ACCAAGACCUGACUUCUAACUAAGUCU ACGUUCC-3' (SEQ ID NO: 22) |

DETAILED DISCLOSURE OF THE INVENTION

The term "about" is used in this patent application to describe some quantitative aspects of the invention, for example, size. It should be understood that absolute accuracy is not required with respect to those aspects for the invention to operate. When the term "about" is used to describe a quantitative aspect of the invention the relevant aspect may be varied by ±10% (e.g., ±1%, ±2%, ±3%, ±4%, ±5%, ±6%, ±7%, ±8%, ±9% or ±10%).

For the purposes of this invention, the binding between two molecules, which is based on specific interactions between specific sites present on the two molecules, is referred to as "specific binding". The specific binding between two entities are scientifically represented by their dissociation constant often less than about $10^{-6}$, less than about $10^{-7}$, or less than about $10^{-8}$ M. Examples of specific binding include, but are not limited to, binding between an antibody and the corresponding antigen based on the interactions between the antigen binding sites present on the antibody and the specific epitopes present on the antigen, binding between an aptamer and its target biomolecule based on the interactions between the target binding sites present on the aptamer and the specific target sites present on the target biomolecule. The target molecule could be a molecule on a cell surface, not necessarily a free entity. Additional examples of specific binding between any two molecules and further aspects of specific binding are well known to a person of ordinary skill in the art.

For the purposes of this invention, the binding between two molecules which is not based on specific interactions between the two molecules is referred to as "non-specific binding". Examples of non-specific binding include, but are not limited to, binding between an antibody and an antigen which is not a target antigen for the antibody and the binding is based on the interactions between the random sites on the antibody and the antigen, binding between an aptamer and a biomolecule which is not the target biomolecule for the aptamer and the binding is based on the interactions between random sites present on the aptamer and the biomolecule. Additional examples of non-specific binding between any two molecules and further aspects of non-specific binding are well known to a person of ordinary skill in the art.

Various aspects of the disclosed invention provide devices and methods for isolation of a target cell from a population of cells. Various embodiments of the devices of the current invention comprise of one or more microfluidic channels and one or more aptamers and one or more antibodies attached to the inner surface of the microfluidic channels, wherein said one or more aptamers and said one or more antibodies are capable of specific binding to one or more biomolecules present on the surface of the target cell.

The disclosed devices and methods provide high capture efficiency and high capture purity of the target cells. Capture efficiency is defined as the ratio of the number of the target cells captured by a device to the number of the target cells present in the total population of cells passed through the device. Capture purity is defined as the ratio of the number of the target cells captured by a device to the total number of cells captured by the device.

Various embodiments provide devices having a capture efficiency of about 80% to about 99%, about 85% to about 95%, or about 90% to about 95%. In certain embodiments, the devices of the current invention provide the capture efficiency of about 90, 91, 92, 93, 94, 95, 96, 97, 98, 99, or 100%. The devices of the current invention also provide the capture purity of about 80% to about 99%, about 85% to about 95%, or about 90% to about 95%. In certain embodiments, the devices of the current invention provide the capture purity of about 90, 91, 92, 93, 94, 95, 96, 97, 98, 99, or 100%.

The current invention provides microfluidic devices to capture and isolate target cells from a population of cells using aptamers and antibodies capable of specifically binding to the molecules present on the surface of the target cells. The microfluidic devices of the current invention comprise:
  a) one or more microfluidic channels, and
  b) one or more aptamers and one or more antibodies attached to the inner surface of said one or more microfluidic channels,
wherein said one or more aptamers and said one or more antibodies are capable of specific binding to one or more biomolecules present on the surface of the target cell.

The devices of the current invention comprise of one or more microfluidic channels. A microfluidic channel has at least one dimension of less than about 1 mm and can be of any desired shape (e.g., circular, a half-circle, D-shaped, square, rectangular, quadrangular, triangular (V-shaped), etc.). For example, if a microfluidic channel has a quadrangular cross section, the width or the height (or both the width and height) of the microfluidic channel is less than 1 mm. The channel can be straight, angled, curved, spiral shaped, connected in a network, or other shapes known to a person of ordinary skill in the art. While the length of the microfluidic channel can be of any desired length, certain embodiments provide for channels having a length of about 10 mm to about 1000 mm, about 20 mm to about 500 mm or about 30 mm to about 100 mm or about 40 mm to about 60 mm.

In various embodiments, the microfluidic channel may be a quadrangular channel that has the width of about 0.1 mm to about 5 mm, about 0.5 mm to about 4 mm, about 1 mm to about 4 mm, or about 2 mm to about 3 mm. In other embodiments of the invention, the microfluidic channel has a depth of about 10 μm to about 1000 μm, about 20 μm to about 500 μm, about 50 μm to about 200 μm, or about 90 μm to about 150 μm. In a further embodiment, the microfluidic channel of the device of the current invention is a flat microfluidic channel having a length of about 50 mm, width of about 2 mm, and depth of about 100 μm.

In other embodiments, the device comprises one or more microfluidic channels that is a circular channel having a diameter of about 20 μm to about 1000 μm, about 50 μm to about 500μ, about 70 μm to about 200 μm, or about 90 μm to about 150 μm. In certain embodiments, the microfluidic channel has a diameter of about 100 μm.

In certain embodiments of the invention, the microfluidic channels contain one or more features that increase the inner surface area of the microfluidic channels thereby increasing the interaction between the target cells and the one or more aptamers and one or more antibodies. Non-limiting examples of the features that increase inner surface area of the microfluidic channels include microposts, micropillars, or a combination thereof. Additional examples of the features that increase the inner surface area of the microfluidic channels are well known to a person of ordinary skill in the art and such embodiments are within the purview of the current invention.

The device of the current invention can be made from silicon, glass, thermoset polymers (e.g., poly(dimethylsiloxane) (PDMS), polyurethane, epoxy, or polyimide), and thermoplastics (e.g., polycarbonate, acrylic such as poly(methyl methacrylate), polyethylene, polypropylene, polystryrene, Teflon, cyclic olefin polymers, co-polymers, or mixtures thereof).

The aptamers and the antibodies can be attached to the inner surface of the microfluidic channels in various ways. In certain embodiments, the aptamers and the antibodies are attached to the inner surface of the microfluidic channels in a covalent manner. Binding in a covalent manner ensures that the aptamers and the antibodies are, for practical purposes, permanently attached to the inner surface of the microfluidic channels which avoids the loss of the aptamers and the antibodies and consequently, avoids the loss of target cells attached to the aptamers and the antibodies. In these embodiments, the target cells are released from the aptamers and the antibodies by providing conditions that cause dissociation of the binding between the target cells and the aptamers and the antibodies.

In other embodiments, the aptamers and the antibodies are attached to the inner surface of the microfluidic channels in a non-covalent manner. In these embodiments, the target cells can be released from the aptamers and the antibodies by providing conditions that cause dissociation of the aptamers and the antibodies from the inner surface of the microfluidic channels. Also, the target cells can be released from the aptamers and the antibodies by providing conditions that cause dissociation of the binding between the target cells and the aptamers and the antibodies but keeping the aptamers and the antibodies attached to the microfluidic channels. Alternately, in these embodiments, the target cells can be released from the aptamers and the antibodies by providing conditions that cause dissociation of the aptamers and the antibodies from the inner surface of the microfluidic channels and dissociation of the binding between the target cells and the aptamers and the antibodies.

In certain embodiments, the aptamers and the antibodies are attached to the inner surface of the microfluidic channels via between one or more agents that are attached to the aptamers and the antibodies and one or more binding partners for the agents that are attached to the inner surface of the microfluidic channels. For example, an agent may be attached to the aptamers and the antibodies; whereas, the binding partner for the agent can be attached to the inner surface of the microfluidic device. Alternately, a first agent may be attached to the aptamer and a second agent may be attached to the antibody; whereas, the binding partner for the first agent and the binding partner of the second agent may be attached to the inner surface of the microfluidic channels. Even further, a plurality of agents may be attached to one or more aptamers and one or more antibodies; whereas, a plurality of binding partners for the plurality of agents can be attached to the inner surface of the microfluidic channels.

In an embodiment of the invention, the aptamers and the antibodies are attached to biotin; whereas, avidin is attached to the inner surface of the microfluidic channels. The aptamers and the antibodies are thus attached to the inner surface of the microfluidic channels through the binding between biotin and avidin. Avidin can be replaced with other molecules that can bind with biotin, for example, streptavidin or NeutrAvidin. In another embodiment of the invention, the aptamers and the antibodies are attached to avidin and biotin is attached to the inner surface of the microfluidic channels. Yet other embodiments provide for the attachment of aptamers to avidin and antibodies to biotin and both avidin and biotin are attached to the inner surface of the microfluidic channels to facilitate coupling of the antibodies and aptamers to the channels. Still other embodiments provide for the attachment of aptamers to biotin and antibodies to avidin and both avidin and biotin are attached to the inner surface of the microfluidic channels to facilitate coupling of the antibodies and aptamers to the channels. The aptamers and the antibodies are thus attached to the inner surface of the microfluidic channels through the binding between biotin and avidin.

Other binding agents include protein A and/or protein G, which are attached to the inner surface of the microfluidic channels. Protein A and protein G can bind with antibodies directly. Aptamers may also be linked with an amino group, and this amino group and the amino groups of present on the antibodies can be attached to carboxyl groups on surfaces through many bifunctional cross-linking molecules. Non-limiting examples of bifunctional cross-linking agents that contain carboxyl groups which can be linked to amine groups include 1-ethyl-3-(3-dimethylaminopropyl) carbodiimide (EDC).

Additional examples of the agents and the binding partners for the agents are well known to a person of ordinary skill in the art can be used to attach the aptamers and the antibodies to the inner surface of the microfluidic channels and such embodiments are within the purview of the current invention. In certain embodiments, the aptamers and the antibodies are attached to the inner surface of the microfluidic channels through a spacer which helps the aptamers and the antibodies to float in the lumen of the microfluidic channels. Aptamers and antibodies floating in the lumen of the microfluidic channels have enhanced interactions with fluids passing through the channels. For example, the linker can be attached to biotin and/or avidin and then coupled to an antibody or aptamer for attachment to a channel in a microfluidic device as disclosed herein.

In an embodiment, the spacer is a polymer, preferably, a biocompatible polymer. Examples of polymers that can be used to as spacers include, but are not limited to, polyethylene glycol (PEG), oligonucleotides, peptides, polyethylene oxide (PEO), polylactic acid (PLA), polyglycolic acid (PGA), polyhydroxybutanoates (PHB), PEG-PLA (polylactide), PEG-PGA (polyglycolide), poly(glycolic-co-lactic acid), polylactones, poly(dioxanone), poly(caprolactone), polyurethane, polyphosphazenes, polyanhydrides, polycarbonates, and polyorthoesters. Additional polymers that can be used to attach the aptamers and the antibodies to the surface of the microfluidic channels are well known to a person of ordinary skill in the art and are within the purview of this invention.

In another embodiment, the spacer contains a cleavable linker. The linker can be cleavable by light (photons), pH, or other physical or chemical means. The linker can also be a specific oligonucleotide sequence that can be cleaved by an enzyme (e.g., deoxyribonuclease for a DNA sequence). Where the linker is a DNA sequence, it can be between about 10 and about 3000 nucleotides in length, optionally about 10 to about 300 nucleotides in length, optionally about 10 to 100 nucleotides in length, optionally about 10, about 20, about 40 or about 80 nucleotides in length; or optionally, any number (integer) between about 10 and about 3000 nucleotides for the length of the linker. As discussed herein, the sequence of the DNA linker can include endonuclease recognition sites that permit cleavage of the DNA linkers to facilitate release of captured cells (e.g., HINDIII which cuts a DNA sequence containing 5'-AAGCTT-3' into 5'A and 5'-AGCTT-3'). Other endonuclease recognition sites known in the art can, likewise, be incorporated into DNA linkers as disclosed herein.

In further embodiments of the invention, the aptamers can be covalently attached to the microfluidic channels; whereas, the antibodies can be non-covalently attached to the microfluidic channels. Similarly, in certain other embodiments, the antibodies can be covalently attached to the microfluidic channels; whereas, the antibodies can be non-covalently attached to the microfluidic channels. Various combinations of non-covalent and covalent attachment can be designed by a person of ordinary skill in the art and such embodiments are within the purview of the current invention.

As described above, in various aspects of the invention, one or more aptamers and one or more antibodies are attached to the inner surface of the microfluidic channels. These aptamers and antibodies specifically bind to biomolecules present on the surface of target cells thereby capturing these cells from the population of cells. The ratio of antibody to aptamer can be between 1:3 to 1:30000, optionally between 1:30 to 3000.

Non-limiting examples of the aptamers include DNA aptamers, RNA aptamers, XNA (nucleic acid analogs or artificial nucleic acids) aptamers, and peptide aptamers. Examples of XNA include, but are not limited to, peptide nucleic acid (PNA), Morpholino and locked nucleic acid (LNA), glycol nucleic acid (GNA), and threose nucleic acid (TNA). In certain embodiments of the invention, the aptamers can be selected from Sgc8, TD05, sgc3b, Sgd5, KH2B05, KH1A02, KH1C12, TLS11a, PP3, TV02, HCH07, KDED2a-3, KCHA10, S11e, DOV4, aptTOV1, KMF2-1a, EJ2, CSC01, SYL3C, Anti-EGFR aptamer, or Anti-PSMA aptamer.

Non-limiting examples of the antibodies include antibodies against protein tyrosine kinase (PTK-7), epithelial cell adhesion molecule (EpCAM), E-cadherin, cytokeratin, zona occludens, laminin-1, entactin, syndecan, mucin-1, desmoplakin, collagen, CD-31, CD-34, CD-117, N-cadherin, vimentin, fibronectin, beta-catenin, integrin, Snail, Slug, forkhead box C2, epidermal growth factor receptor (EGFR), G-protein coupled receptors (GPCR), prostate-specific membrane antigen (PSMA). A person of ordinary skill in the art can select an antibody against a biomolecule present on the surface of the target cell and such embodiments are within the purview of the current invention.

Certain embodiments of the invention provide devices having an aptamer and an antibody attached to the inner surface of the microfluidic channels, wherein the aptamer and the antibody are capable of specific binding to the same biomolecule (e.g. a particular receptor) present on the surface of the target cells. For example, in an embodiment of the invention, aptamer sgc8, which is capable of specific binding to protein tyrosine kinase 7 (PTK-7) and anti-PTK-7 antibody are attached to the inner surface of the microfluidic channels.

Certain other embodiments of the invention provide devices having an aptamer and an antibody attached to the inner surface of the microfluidic channels, wherein the aptamer and the antibody are capable of specifically binding to different biomolecules (e.g. different cell surface receptors) present on the surface of the target cells. Even further embodiments of the invention provide devices having a plurality of aptamers and a plurality of antibodies attached to the inner surface of the microfluidic channels, wherein each of the plurality of aptamers and each of the plurality of antibodies are capable of specifically binding to different biomolecules (e.g. a variety of cell surface receptors) present on the surface of the target cells.

Devices containing aptamers and antibodies that can bind to different biomolecules on the surface of the target cells provide "multivalent binding" of the target cells. "Multivalent binding" indicates that one or more aptamers and one or more antibodies bind to multiple biomolecules on the surface of the target cell. Thus, multivalent binding provides higher affinity and/or avidity as compared to microfluidic channels having aptamers and antibodies binding only to a single biomolecule (e.g., a cell surface receptor) on the target cells. Multivalent binding also provides the capacity to the microfluidic devices of the current invention to capture various types of target cells in a single device thereby broadening the domain of target cells captured in a single run.

Various embodiments of the invention provide devices having aptamers and antibodies capable of specific binding to biomolecules present on the surface of different types of cells (e.g., cell type A, B, C and D). The aptamers and the antibodies capable of specific binding to biomolecules present on the surface of different types of cells can be attached throughout the inner surface of the microfluidic channels.

Alternately, the aptamers and the antibodies capable of specific binding to biomolecules present on the surface of different types of cells can be attached to the inner surface of the microfluidic channels in various zones. For example, e.g., a first zone containing aptamers and antibodies capable of specifically binding to biomolecules on the surface of cell type "A", a second zone specific for cell type "B", a third zone specific for cell type "C", a fourth zone specific for cell type "D", and so on.

The devices of the current invention can further comprise of a micro-mixer or a number of mixers which mix the fluids that pass through the microfluidic channels. The micro-mixer can be a passive micro-mixer or an active micro-mixer. Passive mixers rely on microfeatures created in channels, whereas active mixers use external forces to achieve mixing. Non-limiting examples of micro-mixers that can be used in the devices of the current invention include T- or Y-shaped micro-mixers, parallel lamination micro-mixers, sequential lamination micro-mixers, sequential micro-mixers, focusing enhanced micro-mixers, droplet micro-mixers, pressure field micro-mixers, electrokinetic micro-mixers, dielectrophoretic micro-mixers, electrowetting micro-mixers, magneto-hydrodynamic micro-mixers, ultrasound micro-mixers, asymmetric serpentine micro-mixers, circulation-disturbance micro-mixers, connected-groove micro-mixers, crossing manifold micro-mixers, elecrokinetic instability micro-mixers, electrowetting on dielectrics micro-mixers, magneto hydrodynamic micro-mixers, temperature-induced micro-mixers, planar serpentine micro-mixers, split-and-recombine micro-mixers, slanted-groove micro-mixers, staggered-herringbone micro-mixers, staggered overlapping crisscross micro-mixers, and herringbone groove-based micro-mixers. In an embodiment, the devices of the current invention comprise of a herringbone groove-based micro-mixer. Additional examples of micro-mixer devices are well known to a person of ordinary skill in the art and are within the purview of the current invention.[30]

The devices of the current invention can further comprise of a valve or a number of valves for controlling flow directions, regulating flows, and isolating one region from another in a microfluidic device. The microvalves can be actuated using either passive or active actuation mechanisms, including electric, magnetic, piezoelectric, pneumatic, thermal, and/or phase change.

In various aspects of the invention, the fluid passes through said one or more microfluidic channels at a constant flow rate or a variable flow rate. The flow rate can be about 0.1 to about 50 µL/second, about 0.5 to about 10 µL/second or about 1.0 to about 3.0 µL/second. In one embodiment, the flow rate is about 2.0 µL/second. These flow rates are for the channels with a depth of 100 µm and a width of 2 mm. A larger flow rate may be used to achieve a high-shear flow if the channel dimension is increased.

The current invention also provides methods of isolating target cells from a population of cells. The population of cells can be obtained from a cell culture source or from a subject having a disease (e.g., cancer or a disease caused by a pathogen such as a bacterial cell, yeast cell, or virus). Isolation of target cells from a population of cells according to the methods of current invention comprises:

a) passing the population of cells through microfluidic device of the current invention under conditions that permit the interaction and capture of the target cell by the one or more aptamers and said one or more antibodies attached to the inner surface of one or more microfluidic channels, b) passing a wash buffer through the said one or more microfluidic channels to remove the cells non-specifically bound to the aptamers and the antibodies, c) optionally, passing one or more reagents to verify that the captured cells are truly target cells, d) optionally, enumerating the cells captured, e) optionally, releasing the captured target cell from the scaffolding particle-ligand conjugates, and f) optionally, collecting the released target cell.

In one embodiment, not all of these steps are needed for a certain application. For example, step c is not needed, if target cells are pre-stained or interacted with dye-labeled molecules.

To isolate target cells from a population of cells, the population of cells from a tissue or body fluids of a subject (an individual) can be processed to prepare a sample containing the population of cells. The subject can be an animal, for example, a mammal such as a human, a primate, a bovine, a pig, a feline, a rodent, or a canine. The population of cells can be separated from other components of the body fluids, for example, by centrifugation or filtration. A population of cells from a solid tissue, for example, a tumor, can also be subjected to the methods of the current invention by homogenizing the solid tissue to prepare a slurry or solution containing the population of cells.

In other embodiments, target cells from the blood from a subject (e.g., a human) are isolated according to the methods of current invention after treatment to lyse the RBCs in the blood without damaging the other cellular components in the blood. Detailed procedures for lysis of RBCs without damaging other components of blood are described elsewhere in this application or are known to those skilled in the art.

In another embodiment, target cells from the body fluids of a subject (e.g., a human) are isolated according to the methods of current invention without any processing or pretreatment except for anti-coagulants contained in the tube used for the blood collection. Whole blood can be directly introduced into the device. For example, target cells from unprocessed blood obtained from a human can be isolated according to the methods of current invention. Non-limiting examples of body fluids that can be subjected to the methods of current invention include amniotic fluid, aqueous humor, vitreous humor, bile, cerebrospinal fluid, chyle, endolymph, perilymph, female ejaculate, male ejaculate, lymph, mucus (including nasal drainage and phlegm), pericardial fluid, peritoneal fluid, pleural fluid, pus, rheum, saliva, sputum, synovial fluid, vaginal secretion, and blood.

In an aspect of the invention, the methods of isolating the target cells include washing the microfluidic channels with attached aptamers and the antibodies with solutions under conditions that allow the captured cells that are bound via specific binding to the aptamers and the antibodies to remain captured while causing the cells that are bound via non-specific binding to the aptamers and the antibodies to be released. The types of solutions or other conditions used to wash off cells that are bound to the aptamers and the antibodies via non-specific binding depend on the specificity and type of molecular interactions between the aptamers and the antibodies conjugates and the target cells. Non-limiting examples of conditions that cause only the non-specifically bound cells to be washed off include, but are not limited to, absence/presence and concentration of specific chemicals or biomolecules, surfactants, a buffer such as PBS (phosphate buffered saline), pH of the solution, temperature of the solution, shear stress of washing solution, and a combination of these conditions. Additional examples of the conditions that cause only the non-specifically bound cells to be washed off are well known to a person of ordinary skill in the art and such embodiments are within the purview of the current invention.

In one aspect of the invention, the methods of isolating the target cells comprise releasing the target cells captured by the aptamers and the antibodies. Releasing the target cells captured by the aptamers and the antibodies may comprise treating the complexes of the captured cells with the aptamers and the antibodies under conditions that allow the captured cells to be released. The types of solutions or other conditions used to release the specifically bound target cells depend on the specificity and type of molecular interactions between the captured cells and the aptamers and the antibodies. Non-limiting examples of conditions that cause specifically bound target cells to be released include, but are not limited to, absence/presence and concentration of specific chemicals or biomolecules (for example, enzymes or DNA with complementary sequences), pH of the solution, temperature of the solution, shear stress of washing solution, physical forces (for example, air/water interface), and a combination of these options. Additional examples of conditions that cause specifically bound target cells to be released are well known to a person of ordinary skill in the art and such conditions are within the purview of the current invention.

In an embodiment of the invention, target cells captured by the aptamers and the antibodies are released by treatment with agents that interfere with the interactions between the aptamers and the antibodies with the target cells thereby separating the target cells from the aptamers and the antibodies. For example, target cells bound to the aptamers and the antibodies can be released by treatment with solutions containing high concentration of chemicals capable of disrupting binding between the target cells and the aptamers and the antibodies. An example of a chemical capable of disrupting the interaction between the target cells and the aptamers and the antibodies is a ligand that can specifically bind to the biomolecules on the target cells on the same site where the aptamers and/or the antibodies bind. Another example of a chemical capable of disrupting the interaction between target cells and the aptamers and the antibodies is a ligand that can cause a conformation change in the aptamer and/or the antibody or the target biomolecule thereby releasing the target cells. An even further example of a chemical capable of disrupting the interaction between target cells and the aptamers and the antibodies is a compound that can bind to the aptamers and/or the antibodies on the same site through which the aptamers and/or the antibodies bind to the target cells.

Other embodiments provide for the release of target cells captured by the aptamers and the antibodies by treatment with chemicals that sever the interaction between the aptamers and the antibodies and the inner surface of the microfluidic channels thereby releasing the target cells from the microfluidic channels. For example, target cells captured by the aptamers and the antibodies can be released by treatment with peptidases that cleave the peptide aptamers or nucleases that cleave the nucleotide aptamers thereby releasing the captured cells from the aptamers. In another embodiment of the invention, the target cells can be released by other physical or chemical means. For example, air or other gas can be used to force the detachment of cells from the scaffold due to the amount of force exerted by the air/liquid interface.

In another embodiment of the invention, a cleavable linker is contained in the spacer linking the aptamers and the antibodies to the inner surface of the microfluidic channels. For example, the linker can be photocleavable and the target cells can be released by using UV light exposure, which have minimal effect on cell viability. A pH cleavable linker can also be used, though it is ideally used under conditions that will not affect cell viability. In the situation where cell viability is not critical (e.g., only genetic analysis is to be performed), a strong acid or base can be used.

In yet another embodiment of the invention, where biotin-avidin are used to attach the aptamers and the antibodies to the inner surface of the microfluidic devices, excess amounts of biotin or avidin can be used to release the target cells. In another embodiment of the invention, target cells can be released by DNA hybridization with aptamers. Various combinations of linkers (e.g., photocleavable, pH cleavable, protease cleavable and/or endonuclease cleavable linkers) can be used to attach ligands to a particle.

Materials and Methods

Cells and Cell Culture

T-cell human acute lymphoblastic leukemia cells (CCRF-CEM cells, CCL-119) and B-cell human Burkitt's lymphoma cells (Ramos cells, CRL-1596) were purchased from American Type Culture Collection (ATCC). Antigen expression of the cell surface was confirmed by flow cytometry. All cells used in the experiments were maintained in incubators at 37° C. with 5% $CO_2$. CEM and Ramos cells were grown in RPMI 1640 medium (ATCC) supplemented with 100-units/mL antibiotic-antifungal solutions of penicillin-streptomycin (Cellgro, Manassas, Va., USA) and 10% fetal bovine serum (FBS; heat-inactivated; Gibco). Just before use, cells were washed three times with 2 mL Dulbecco's phosphate-buffered saline with calcium and magnesium ions (PBS) (Fisher Scientific, Pittsburgh, Pa., USA). Cell concentrations were determined using a hemocytometer before each experiment. Specific cell concentrations are detailed in the figure captions. A solution of 1% (w/v) bovine serum albumin (BSA) (Fisher) and 0.05% (w/v) Tween-20 (Fisher) in PBS was used for re-suspending cells for cell captures.

Design and Fabrication of Microfluidic Devices

The eight channels were connected to form a high throughput device.[10, 14, 17] We designed each channel with a length of 50 mm, a width of 2.1 mm, and a depth of 100 µm. The distance between the micropillars is 60 µm and each pillar's diameter is 90 µm. The devices were made of polydimethylsiloxane (PDMS) and bonded to a glass slide. PDMS devices were fabricated using soft lithography.[31] The layout of the device was first designed in AutoCAD, and a high-resolution transparency photomask was printed. The master used to create the fluidic channels was made by spin coating a layer of SU-8 2035 photoresist (MicroChem, Newton, Mass., USA) on silicon wafers (Silicon Inc., Boise, Id., USA) using a spin coater (Laurell Tech., North Wales, Pa., USA). Followed by UV exposure and development, a silicon master patterned with the complementary structures of the photomask was created. The channel depth was controlled by the spin speed of the SU-8, and measured with a Dektak 150 profilometer. PDMS layer was obtained by casting a liquid PDMS precursor (Dow Corning, Midland, Mich., USA) against the silicon master. The PDMS layer was cured in an 80° C. oven for 50 minutes. It was later removed from the master and snatch edges were removed. The PDMS layer was then sealed with a glass slide (3 inch×1 inch), and the fluidic channel was generated. The inlet and outlet holes were introduced onto the PDMS layer at the end of the channel. The PDMS chip could be reused after cleaning with suitable solvent.

Affinity Surface Preparation

Figure 6A:
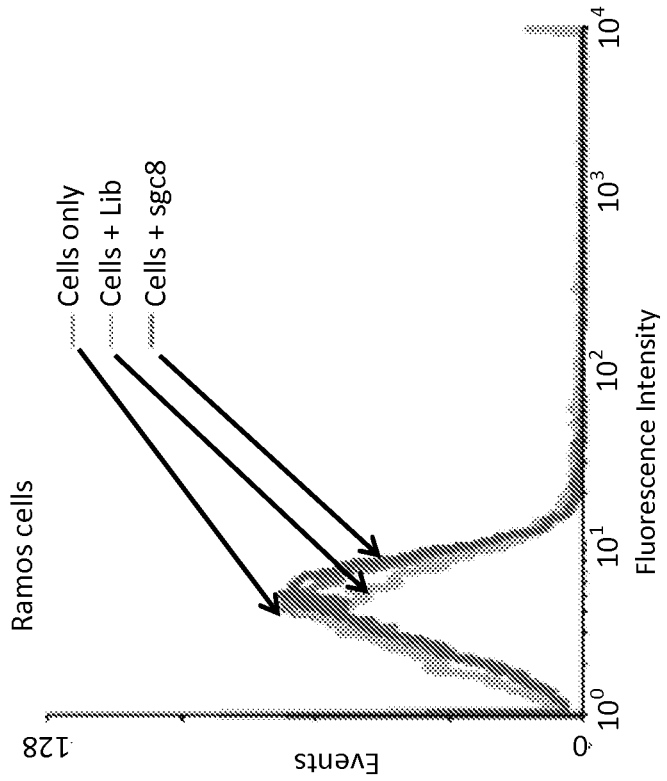
FIGS. 6A and 6B. Flow cytometer testing of the specific binding of CCRF-CEF cells and sgc8 aptamers. (a) sgc8 aptamers selectively bind to CEM cells; negligible signal change was observed for cells incubated with random DNA library (Lib). (b) sgc8 aptamers did not bind to Ramos cells.
Figure 6B:
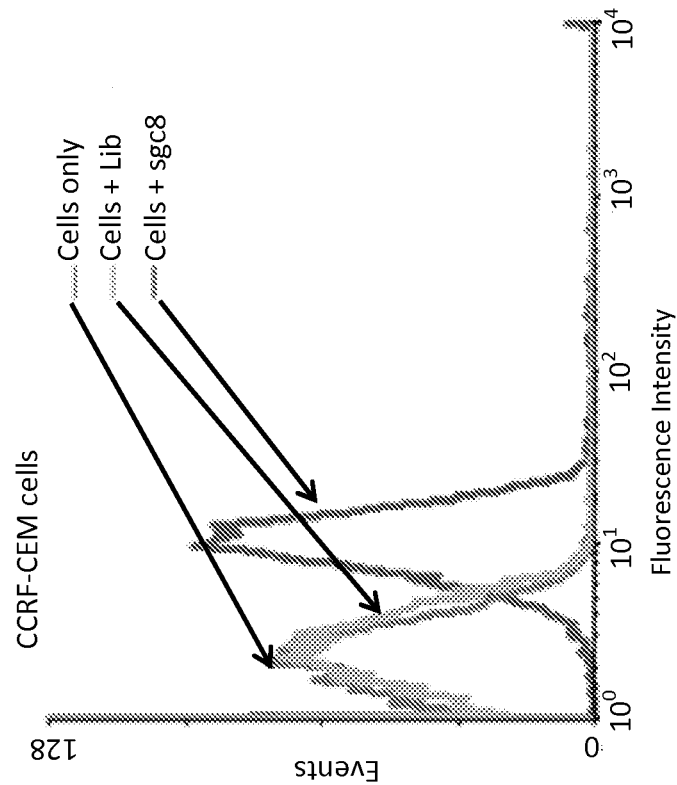

First, the channels were rinsed with 300 µL ethanol at a flow rate of 2 µL/s using a Micro4™ syringe pump (World Precision Instruments, Sarasota, Fla., USA) with a 1 mL syringe connecting to the inlet of the device using polymer tubing. Then, the device was washed with 300 µL PBS buffer at 2 µL/s and 100 µL of avidin (Invitrogen, Carlsbad, Calif., USA) with a concentration of 1 mg/mL was dropped on the inlet. It was introduced then by applying vacuum to the outlet of the device with very low pressure and incubated for 15 min at room temperature. The avidin on the surface was immobilized by physical adsorption. Next, biotinylated anti-PTK7 (Miltenyi Biotec, Auburn, Calif., USA) and biotinylated sgc8 aptamer solution in PBS containing 1% (w/v) bovine serum albumin BSA and 0.05% (w/v) Tween-20 were added to the devices. The solution was incubated in the channel for 15 min at room temperature. The device was then rinsed with 300 µL of PBS buffer containing 1% (w/v) BSA and 0.05% (w/v) Tween-20. At room temperature, through biotin-avidin interaction, the capture agent (sgc8 aptamer and anti-PTK7 antibody) was introduced onto the substrates, enabling a highly efficient cell capture at high flow rate due to the size-different effect of binding reagent. The aptamer, sgc8 was prepared using previously reported method.[32] Flow cytometry was used to verify their specific bindings with the targeted CEM cells (FIG. 6).

Assembling of the Antibody and the Aptamer Containing Microfluidic Channels

Different mixtures of antibodies and aptamers were used for preparation of microfluidic devices having the aptamer and the antibody attached to the inner surface of the microfluidic channels (Table 1).

TABLE 1

Ratio of aptamer to antibody in various embodiments of the current invention.

| Antibody to aptamer ratio (Anti-PTK7 to sgc8) | Anti-PTK7 (µg/mL) | sgc8 (µM) |
|---|---|---|
| 1:30 | 5 | 1 |
| 1:300 | 5 | 10 |
| 1:3000 | 0.5 | 10 |

Cell Capture Using Aptamer or Antibody Alone

Cell capture: To start the cell capture experiments, the device was first assembled with sgc8 aptamer and anti-PTK7 antibody combination on the surface of microchannel, followed by three rinses with the PBS containing 1% BSA and 0.05% Tween-20. Finally, 1 mL of DiO (green) stained CEM cell suspension in PBS buffer was continuously pumped into the device. Afterwards, the device was washed three times with PBS to remove nonspecifically captured cells, followed by acquiring fluorescent images to determine the cell numbers. The device was placed on the stage of an Olympus IX71 fluorescence microscope (Olympus America, Melville, N.Y., USA) for image acquisition. After cell capturing and rinsing, sets of images corresponding to the green fluorescent cells, red fluorescent cells, and transmission images were acquired at different positions in each channel to determine cell numbers. Then, software Image Pro Plus (IPP) was used for cell counting. Cell counts were further confirmed by comparing fluorescent images with transmission images to get those real target cells with appropriate cell morphology in the transmission images. The cell capture efficiency was calculated by dividing the number of the target cells captured by the number of total target cells introduced into the device, while the purity of cell captured was determined via dividing the number of the captured target cells by the number of the total captured cells, which included target cells and the unspecific bound cells.

Figure 7:
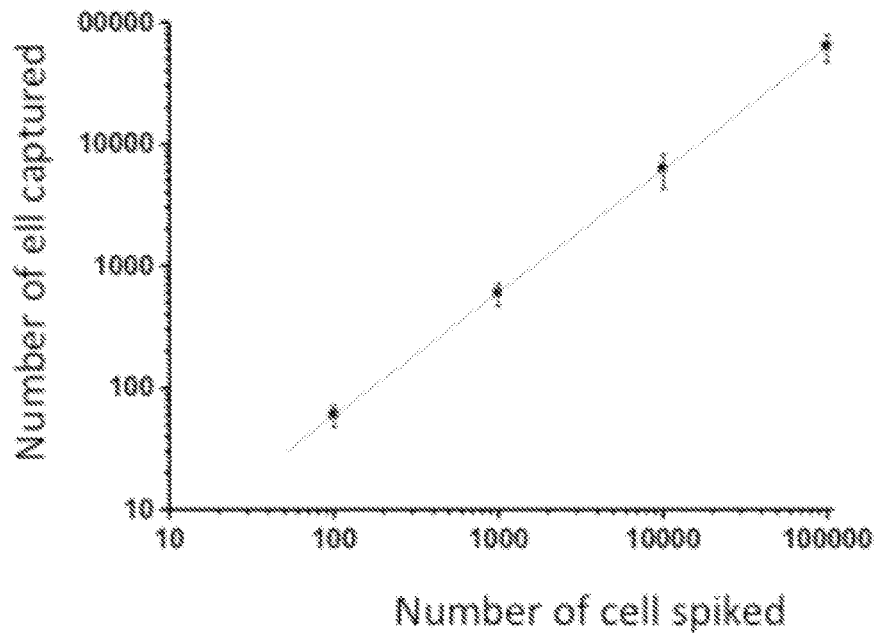
FIG. 7. Calibration curve obtained by using anti-PTK7 alone for 100,000, 10,000, 1,000, and 100 CEM cells spiked in 1 ml PBS buffer with flow rate of 2.0 μL/s.

When capturing CEM cells using antibodies alone, 5 µg/mL anti-PTK7 was immobilized on the channel surface at a flow rate of 2.0 µL/s. CEM cell samples in PBS buffer ranging from $10^2$/mL to $10^5$/mL were used for cell capture. The capture efficiency is (60±4) % (FIG. 7).

Figure 8:
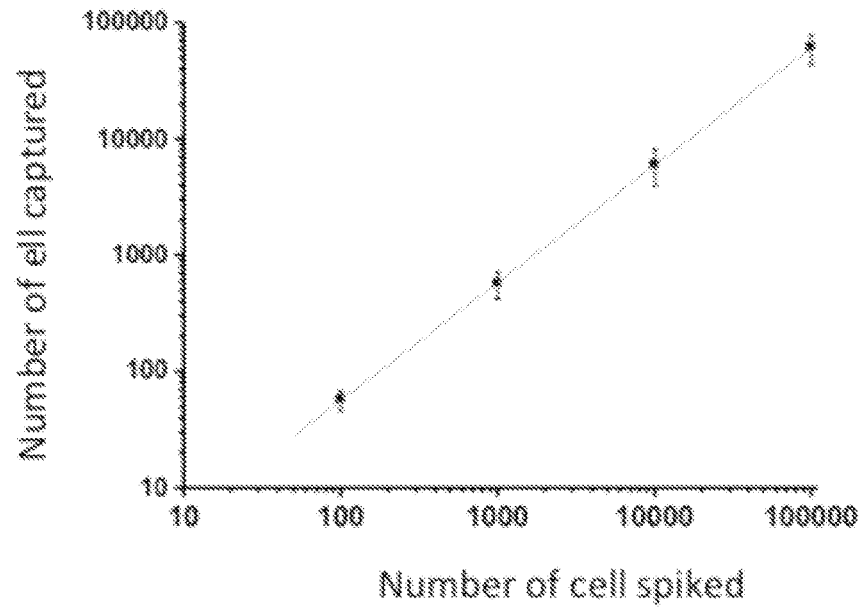
FIG. 8. Calibration curve obtained by using sgc8 aptamer alone for 100,000, 10,000, 1,000, and 100 CEM cells spiked in 1 ml PBS buffer with flow rate of 2.0 μL/s.

The same cells capturing tests using 20 µM sgc8 aptamer alone generated a capture Efficiency of (58±6) % (FIG. 8).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Isolation of Human Leukemia Cells (CCRF-CEM) Using SGC8 Aptamers and Anti-PTK7 Antibodies A microfluidic device to isolate human leukemia cells (CCRF-CEM) using a combination of sgc8 aptamers and anti-PTK7 (protein tyrosine kinase-7) antibodies is provided. These aptamers and antibodies exhibit strong binding to receptor PTK7 which is over expressed on many human cancer cells (including CCRF-CEM cells).[25] The average recovery is above 90% at various cell concentrations. In addition, this method can be used for other types of cell isolation and subsequent molecular analysis, which can facilitate developing effective chemotherapeutic drugs.

Antibodies and aptamers are assembled together onto microfluidic channel surface to form a surface having aptamers and antibodies providing multivalent binding. The affinity surface inside the microfluidic device was prepared using established method of avidin and biotin reactions.[13] We strategically mixed biotinylated anti-PTK7 antibodies (Miltenyi Biotec, Auburn, Calif., USA) and biotinylated sgc8 aptamers together and introduced them to an avidin-immobilized surface (FIG. 1a). The specific binding of our homemade aptamers and target CCRF-CEM cells was verified with flow cytometry (Supporting information). To examine the effect of combination capture on the cell capture, we first compared the capture efficiency of the combination capture with antibody alone capture at a flow rate of 1.2 µL/s. Results showed that both the capture efficiency and purity of combination capture is higher than the antibody alone (FIG. 1). Immediately before cell capturing experiments, cells were washed with PBS and resuspended at concentration of $10^6$ cells/mL. CEM and Ramos cells were stained respectively with Vybrant DiO (green) and DiI (red) cell-labeling solutions (Invitrogen, Carlsbad, Calif., USA). Then the cells were washed with PBS, and resuspended in PBS containing BSA and Tween-20. Flow control in this experiment was achieved using syringe pumps. The syringe holding the cell suspension was connected to the device using polymer tubing.

A feature of the antibody and aptamer combination is its versatility. Specifically, the density of the capture reagent on a substrate can be easily tuned by varying the ratio of antibody to aptamer. Microfluidic devices containing eight parallel channels with micropillar array inside were used in certain embodiments (FIG. 2). To verify the successful assemble of the antibody-aptamer combination, the capture efficiency of different mixtures of anti-PTK7 and sgc8 aptamer immobilized device was studied. Mixtures containing different ratio of antibody to aptamer were prepared. Each mixture was used for surface immobilization. The capture efficiency of each mixture at different flow rates ranging from 1.0 µL/s to 3.0 µL/s was compared (FIG. 2). Under flow rate ranging from 1.0 to 3.0 µL/s, the ratio with 1:300 containing 5.0 µg/mL antibody and 10 µM aptamer showed high capture efficiency all the time. We used this ratio for the following cell capture studies.

Figure 3A:
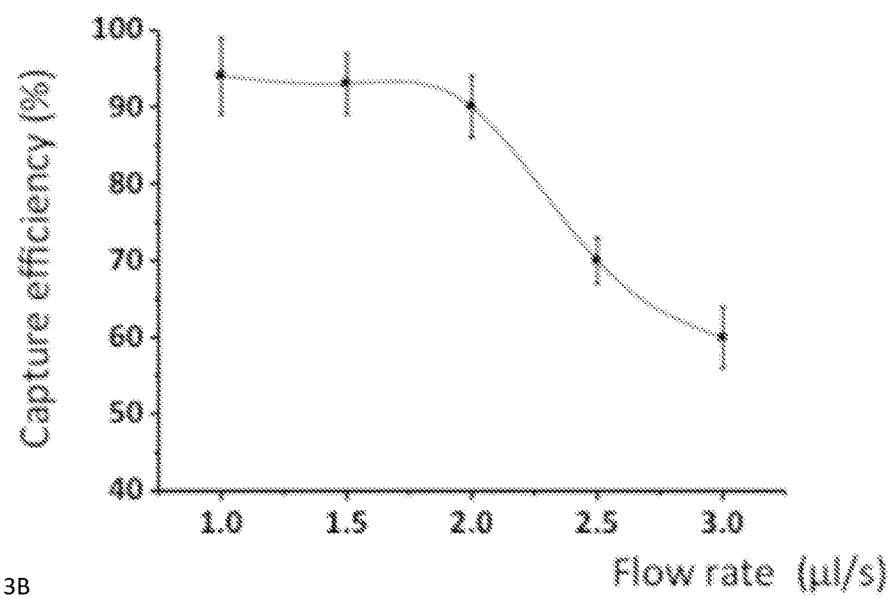
FIGS. 3A and 3B. (a) Cell capture efficiency in PBS at flow rates from 1.0 to 3.0 µL/s using antibody and aptamer combination. (b) Capture purity of target CEM cells at the same flow rate using antibody and aptamer combination; no significant difference was observed. Error bars represent standard deviations (n=3).
Figure 3B:
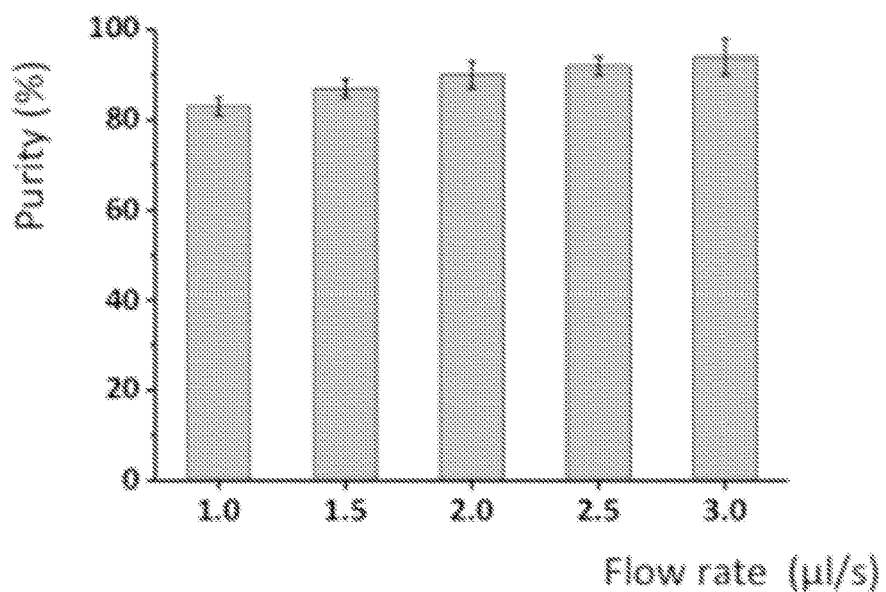

After we confirmed the successful assembling of the combination on the microfluidic surface, we conducted a cell-capture assay under controlled dynamic flow conditions on the device to determine the minimum time required to achieve cell capture. We examined the cell capture performances of the combination at different flow rates. Flow rates ranging from 1.0 µL/s to 3.0 µL/s of the system was varied and cell capture efficiency and purity were compared. As shown in FIG. 3, capture efficiency of CEM cells decreases as the flow rate increases. Flow rates under 2.0 µL/s enable both high capture efficiency and purity using antibody-aptamer combination. An optimal flow rate can be determined for various embodiments based on the resulting cell-capture efficiency.

Figure 4A:
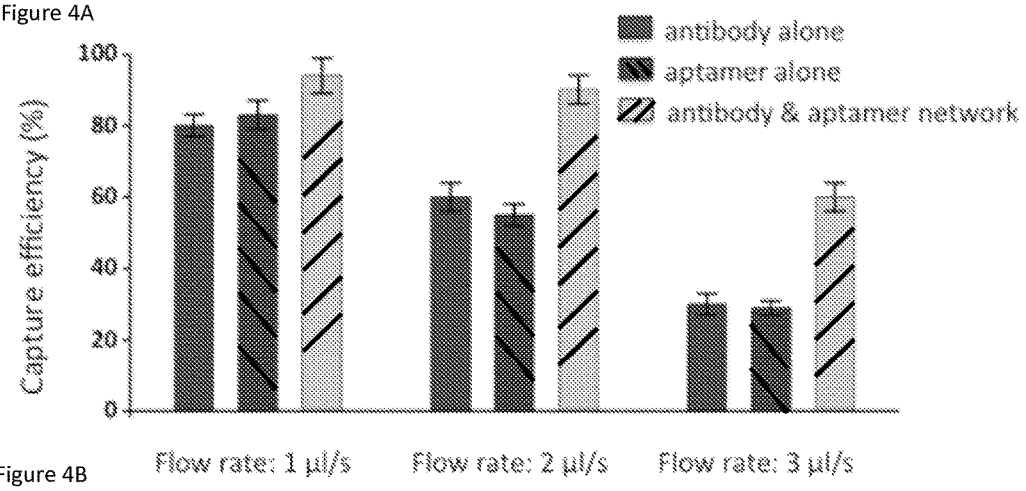
FIGS. 4A and 4B. Comparison of capture of target cells using a combination of antibodies and aptamers with the capture using antibody or aptamer alone: (a) capture efficiency of target CEM cells in PBS buffer at various flow rates ranging from 1.0 to 3.0 µL/s using anti-PTK7 antibody alone, aptamer alone, and a combination of antibody and aptamer; (b) capture purity at the same flow rates. Error bars represent standard deviations (n=3).
Figure 4B:
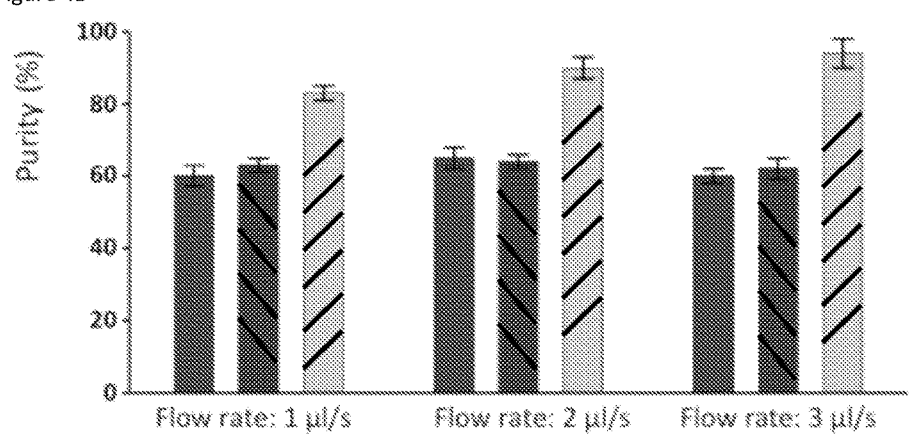

Control experiments using identical devices and conditions with antibody or aptamer alone were then conducted. Remarkably, higher capture efficiencies and purities were obtained using aptamer and antibody together than antibody or aptamer alone, especially at high flow rates. As shown in FIG. 4, the capture efficiency of CEM cells using anti-PTK7 is comparable with aptamer alone, but significantly less than antibody-aptamer combination, especially at high flow rate. This also indicates that the combination of aptamer and antibody captures cells at a much higher shear stress than the monovalent substrate. This can be because the substrate surface of the antibody and aptamer combination has better interactions with the target cells. Monovalent antibody- or aptamer-immobilized substrates provide low capture efficiency at higher shear stress.[9, 27-28] Thus, compared to existing approaches, the combination of aptamer and antibody as provided in the current invention can be used to process larger sample volumes in a shorter time.

To test the cell capture performance of the combination at low concentrations, various cell suspensions containing 10 to $10^3$ cells/mL of a PTK7-positive CEM cell line in PBS buffer were prepared. Results showed the combination of aptamer and antibody provided a capture efficiency of >90% for all cell suspensions.

To enable the efficient capture of CTCs from whole blood, we introduced anti-PTK7 antibodies and sgc8 aptamer combination into a micropillar-based microfluidic device. A series of artificial CTC blood samples were prepared by spiking different concentrations of CEM cells into human blood (Novi, Mich., USA), with the anticoagulant ethylenediaminetetraacetic acid (EDTA). Different concentrations of CEM cells stained in red color were then spiked in whole blood. To test the purity of captured cells from whole blood, DAPI (4,6-diamidino-2-phenylindole, Invitrogen) was introduced into the device to label the nonspecifically captured white blood cells after cell capture and rinsing. As shown in FIG. 5a, the target CEM cells were those positive to both DAPI and DiI (blue merged with red), while cells positive to DAPI only were white blood cells (blue only). A purity of 63±4% was obtained when capturing CEM cells from whole blood, with a capture efficiency of 91±3%. This capture purity from whole blood is much higher than those reported in the literature.[9, 20]

Figure 5B:
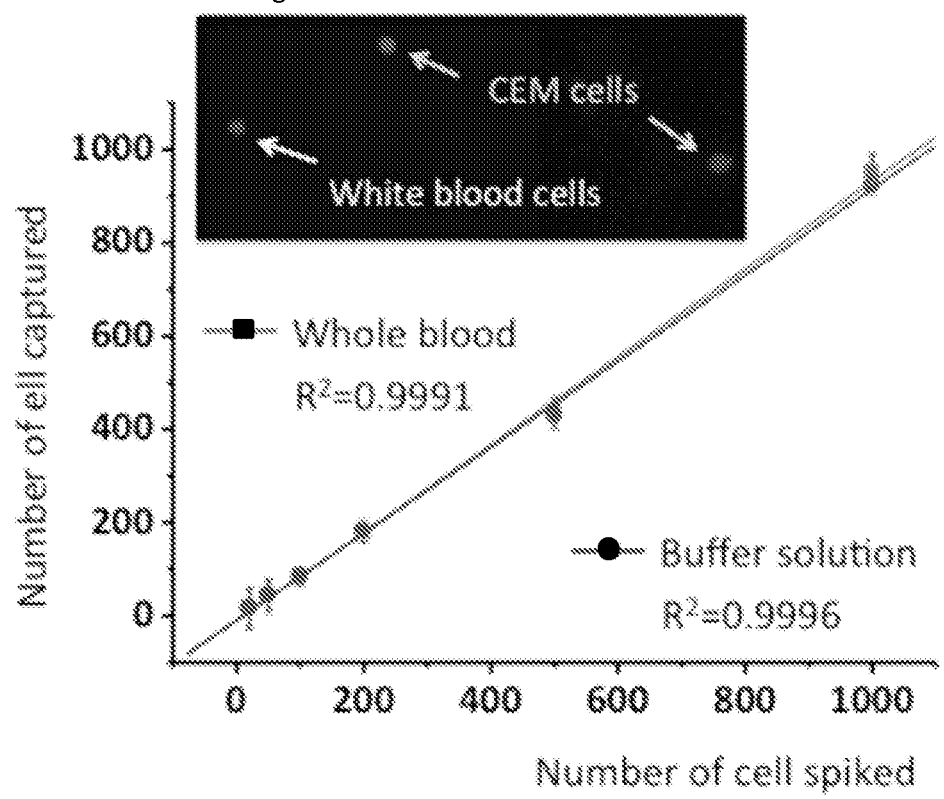

The combination of aptamer and antibody generates a multivalent binding effect on the microfluidic channel surface, which significantly enhances the interactions between cell surface and device substrate, leading to higher capture efficiency. To test the limit of detection for the antibody-aptamer combination cell capture system, cell spike numbers from 1000 to 10 were explored, and >90% capture efficiency was obtained for all cases at the flow rate of 2.0 μL/s (FIG. 5b). This suggests that combination immobilized substrate is effectively bound with the CEM cells with different levels. In addition, with a flow rate of 2.0 μL/s (7.2 mL/h), 1 mL of blood sample can be processed within 15 min, which gives sufficient throughput for clinical applications. The system gives more benefit at higher flow rates and maintains a target cell capture efficiency of >60% for all flow rates up to 3.0 μL/s. Compared with reported work, this antibody-aptamer combination modified device enables >90% capture at a flow rate of 7.2 mL/h, much higher than previously reported. These results show that the combination of aptamer and antibody provides great potential for clinical CTC isolation and enumeration.

Example 2—Control Experiments for "An Ensemble of Aptamers and Antibodies for Multivalent Capture of Cancer Cells"

TDO5 is the aptamer that has specific bind with Ramos cells. This aptamer was used as negative control aptamers for CEM capture using antibody-aptamer ensemble. The binding properties of TDO5 to CEM and Ramos were studied[14]. Studies also indicated that CEM cells do not bind with EpCAM.[33] This antibody was used as negative control antibodies for CEM capture using antibody-aptamer ensemble.

Cell Capture with Ensemble of Anti-PTK7 and TDO5

Figure 9A:
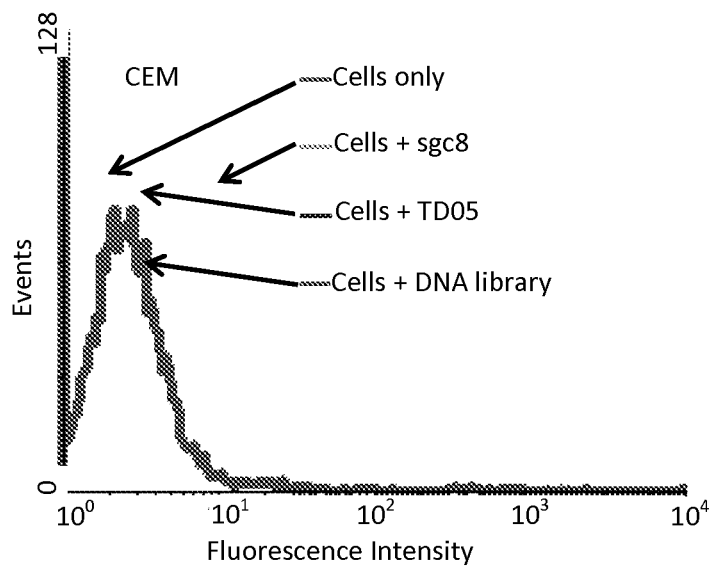
FIGS. 9A and 9B. Flow cytometry histograms showing the selective binding of target cells with corresponding aptamers.
Figure 9B:
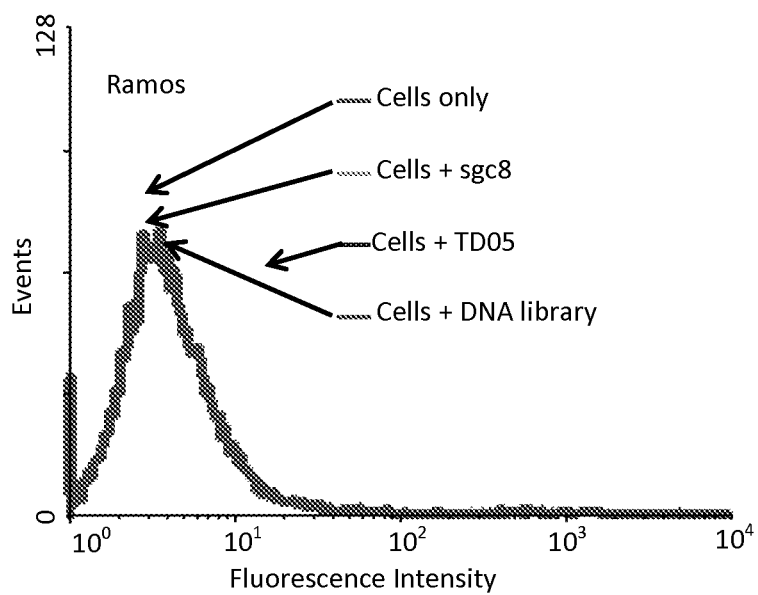

For CEM cells, the capturing reagent is anti-PTK7, while TDO5 was a negative control aptamer; for Ramos cells, TDO5 was the capturing reagent, and anti-PTK7 was the negative control. The capture efficiency of both CEM cells and Ramos cells were about 60% at flow rate of 1 μL/s (FIGS. 9A and 9B).

Cell capture with ensemble of anti-EpCAM and sgc8.

Figure 10A:
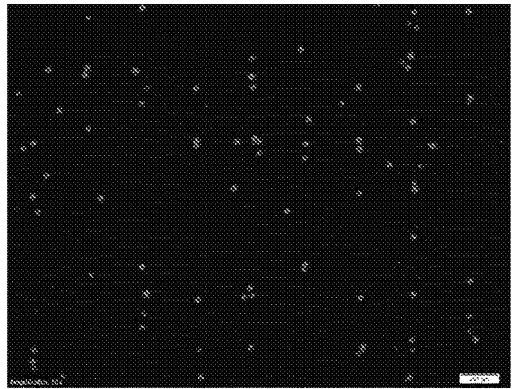
FIGS. 10A and 10B. CEM cells (red.
Figure 10B:
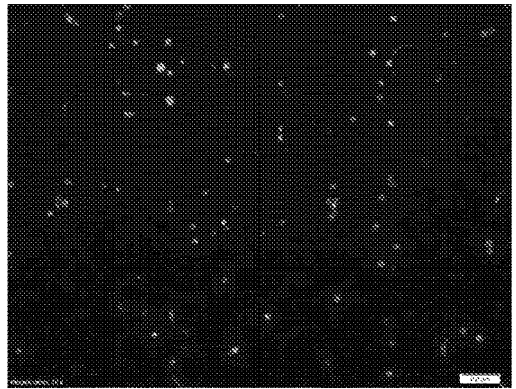

For CEM cells, the capturing reagent is sgc8, while EpCAM was a negative control antibody; for Ramos cells, there was no bind reagent. The capture efficiency of CEM cells was about 60% at flow rate of 1 μL/s. The capture efficiency of Ramos cells were <10% at flow rate of 1 μL/s (see FIGS. 10A and 10B).

Comparison of cell capture with different ensembles.

Figure 11A:
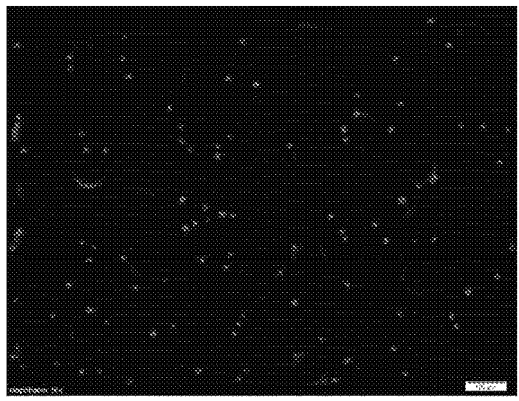
FIGS. 11A and 11B. CEM cells (red.
Figure 11B:
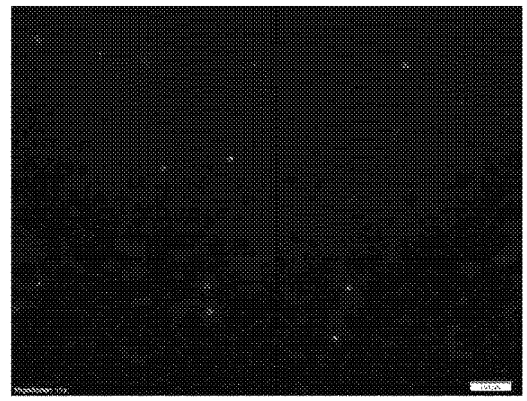
Figure 12:
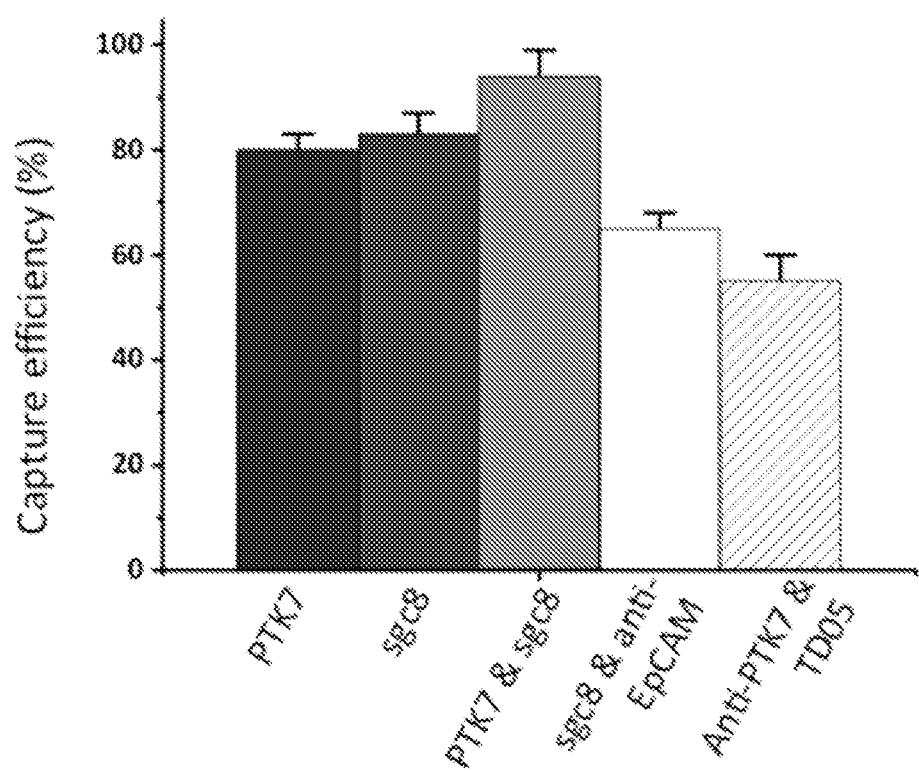
FIG. 12. Results of CEM cell capture using anti-PTK7, sgc8, anti-PTK7 and sgc8 ensemble, anti-EpCAM and sgc8, and anti-PTK7 and TD05.

FIGS. 11A and 11B compare CEM cell capture using anti-PTK7, sgc8, anti-PTK7 and sgc8 ensemble, anti-EpCAM and sgc8, and anti-PTK7 and TD05.

The cell capture was performed at flow rate of 1 μL/s. The results indicate that the ensemble with control antibodies or aptamers showed lower captures ability than the antibody or aptamer alone. In those cases, insufficient capture reagents were immobilized on the surface resulting in fewer captured cells (FIGS. 11A and 11B). These results clearly validate the enhanced multivalent binding of an antibody-aptamer ensemble when both the aptamer and antibody have specific binding with the target cells. If only one capture agent (either aptamer or antibody) has specific binding, its mixture with another reagent that has no specific binding will not have an enhancement effect in the cell capture efficiency.

In conclusion, certain embodiments of the current invention provides devices and methods that show enhanced capture of cancer cells in unprocessed peripheral blood using a combination of aptamer and antibody in a micropillar-based microfluidic device. The unique geometry of the multivalent affinity on the channel surface resulted in the high-performance cell isolation at high flow rates. The advantages of our method include rapid analysis, easy modification of channel surface, and low detection limit. As a result, this platform can be used for cancer diagnosis, prognosis, and monitoring the progress of therapeutic treatment and other clinical applications.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. S. Maheswaran, L. V. Sequist, S. Nagrath, L. Ulkus, B. Brannigan, C. V. Collura, E. Inserra, S. Diederichs, A. J. Iafrate, D. W. Bell, S. Digumarthy, A. Muzikansky, D. Irimia, J. Settleman, R. G. Tompkins, T. J. Lynch, M. Toner, D. A. Haber, New Engl J Med 2008, 359, 366-377.
2. K. Pantel, R. H. Brakenhoff, B. Brandt, Nat Rev Cancer 2008, 8, 329-340.

3. W. Sheng, T. Chen, W. Tan, Z. H. Fan, Acs Nano 2013, 7, 7067-7076.
4. M. X. Zhao, P. G. Schiro, J. S. Kuo, K. M. Koehler, D. E. Sabath, V. Popov, Q. H. Feng, D. T. Chiu, Anal Chem 2013, 85, 2465-2471.
5. J. H. Myung, K. A. Gajjar, J. Saric, D. T. Eddington, S. Hong, Angew, Chem Int Ed Engl 2011, 50, 11769-11772.
6. P. Helo, A. M. Cronin, D. C. Danila, S. Wenske, R. Gonzalez-Espinoza, A. Anand, M. Koscuiszka, R. M. Vaananen, K. Pettersson, F. K. Chun, T. Steuber, H. Huland, B. D. Guillonneau, J. A. Eastham, P. T. Scardino, M. Fleisher, H. I. Scher, H. Lilja, Clinical chemistry 2009, 55, 765-773.
7. J. Guo, F. Yao, Y. Lou, C. Xu, B. Xiao, W. Zhou, J. Chen, Y. Hu, Z. Liu, J Clin Gastroenterol 2007, 41, 783-788.
8. S. Riethdorf, H. Fritsche, V. Muller, T. Rau, C. Schindibeck, B. Rack, W. Janni, C. Coith, K. Beck, F. Janicke, S. Jackson, T. Gornet, M. Cristofanilli, K. Pantel, Clin Cancer Res 2007, 13, 920-928.
9. U. Dharmasiri, M. A. Witek, A. A. Adams, S. A. Soper, Annu Rev Anal Chem 2010, 3, 409-431.
10. S. Nagrath, L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber, M. Toner, Nature 2007, 450, 1235-1239.
11. A. A. Adams, P. I. Okagbare, J. Feng, M. L. Hupert, D. Patterson, J. Gottert, R. L. McCarley, D. Nikitopoulos, M. C. Murphy, S. A. Soper, Journal of the American Chemical Society 2008, 130, 8633-8641.
12. J. P. Gleghorn, E. D. Pratt, D. Denning, H. Liu, N. H. Bander, S. T. Tagawa, D. M. Nanus, P. A. Giannakakou, B. J. Kirby, Lab on a chip 2010, 10, 27-29.
13. Y. Xu, J. A. Phillips, J. L. Yan, Q. G. Li, Z. H. Fan, W. H. Tan, Anal Chem 2009, 81, 7436-7442.
14. W. Sheng, T. Chen, R. Katnath, X. Xiong, W. Tan, Z. H. Fan, Anal Chem 2012, 84, 4199-4206.
15. S. Wang, G. E. Owens, H. R. Tseng, Methods Mol Biol 2011, 726, 141-150.
16. K. Hoshino, Y. Y. Huang, N. Lane, M. Huebschman, J. W. Uhr, E. P. Frenkel, X. Zhang, Lab on a chip 2011, 11, 3449-3457.
17. A. E. Saliba, L. Saias, E. Psychari, N. Minc, D. Simon, F. C. Bidard, C. Mathiot, J. Y. Pierga, V. Fraisier, J. Salamero, V. Saada, F. Farace, P. Vielh, L. Malaquin, J. L. Viovy, Proceedings of the National Academy of Sciences of the United States of America 2010, 107, 14524-14529.
18. S. D. Mikolajczyk, L. S. Millar, P. Tsinberg, S. M. Coutts, M. Zomorrodi, T. Pham, F. Z. Bischoff, T. J. Pircher, Journal of oncology 2011, 2011, 252361.
19. S. Wang, K. Liu, J. Liu, Z. T. Yu, X. Xu, L. Zhao, T. Lee, E. K. Lee, J. Reiss, Y. K. Lee, L. W. Chung, J. Huang, M. Rettig, D. Seligson, K. N. Duraiswamy, C. K. Shen, H. R. Tseng, Angew. Chem. Int. Ed. 2011, 50, 3084-3088.
20. U. Dharmasiri, S. K. Njoroge, M. A. Witek, M. G. Adebiyi, J. W. Kamande, M. L. Hupert, F. Barany, S. A. Soper, Anal Chem 2011, 83, 2301-2309.
21. S. L. Stott, C. H. Hsu, D. I. Tsukrov, M. Yu, D. T. Miyamoto, B. A. Waltman, S. M. Rothenberg, A. M. Shah, M. E. Smas, G. K. Korir, F. P. Floyd, A. J. Gilman, J. B. Lord, D. Winokur, S. Springer, D. Irimia, S. Nagrath, L. V. Sequist, R. J. Lee, K. J. Isselbacher, S. Maheswaran, D. A. Haber, M. Toner, Proceedings of the National Academy of Sciences of the United States of America 2010, 107, 18392-18397.
22. W. Han, B. A. Allio, D. G. Foster, M. R. King, Acs Nano 2010, 4, 174-180.
23. X. Zheng, L. S. Cheung, J. A. Schroeder, L. Jiang, Y. Zohar, Lab on a chip 2011, 11, 3269-3276.
24. S. Wang, H. Wang, J. Jiao, K. J. Chen, G. E. Owens, K. Kamei, J. Sun, D. J. Sherman, C. P. Behrenbruch, H. Wu, H. R. Tseng, Angew. Chem. Int. Ed. 2009, 48, 8970-8973.
25. W. Q. Chen, S. N. Weng, F. Zhang, S. Allen, X. Li, L. W. Bao, R. H. W. Lam, J. A. Macoska, S. D. Merajver, J. P. Fu, Acs Nano 2013, 7, 566-575.
26. M. B. O'Donoghue, X. L. Shi, X. H. Fang, W. H. Tan, Anal Bioanal Chem 2012, 402, 3205-3209.
27. S. T. Wang, H. Wang, J. Jiao, K. J. Chen, G. E. Owens, K. I. Kamei, J. Sun, D. J. Sherman, C. P. Behrenbruch, H. Wu, H. R. Tseng, Angew Chem Int Edit 2009, 48, 8970-8973.
28. J. A. Phillips, Y. Xu, Z. Xia, Z. H. Fan, W. H. Tan, Anal Chem 2009, 81, 1033-1039.
29. U. Dharmasiri, M. A. Witek, A. A. Adams, S. A. Soper, Annu Rev Anal Chem (Palo Alto Calif.) 2010, 3, 409-431.
30. Capretto, L.; Cheng, W.; Hill, M.; and Zhang, X., Micromixing within microfluidic devices, Topics in Current Chemistry, 2011, 304, 27-68.
31. K. T. Kotz, W. Xiao, C. Miller-Graziano, W. J. Qian, A. Russom, E. A. Warner, L. L. Moldawer, A. De, P. E. Bankey, B. O. Petritis, D. G. Camp, 2nd, A. E. Rosenbach, J. Goverman, S. P. Fagan, B. H. Brownstein, D. Irimia, W. Xu, J. Wilhelmy, M. N. Mindrinos, R. D. Smith, R. W. Davis, R. G. Tompkins, M. Toner, Nat Med 2010, 16, 1042-1047.
32. S. K. Sia, G. M. Whitesides, Electrophoresis, 2003, 24, 3563-3576.
33. S. Yamamura et al., PloS ONE, March 2012, 7(3), e32370, pp. 1-8.

We claim:

1. A device for isolating a target cell from a population of cells, the device comprising:
   a) one or more microfluidic channels, and
   b) one or more aptamers and one or more antibodies attached to the inner surface of said one or more microfluidic channels,
   wherein said one or more aptamers and said one or more antibodies are capable of specific binding to one or more biomolecules present on the surface of the target cell.

2. The device of claim 1, wherein said one or more aptamers are selected from DNA aptamers, RNA aptamers, XNA aptamers, or peptide aptamers.

3. The device of claim 2, wherein said one or more aptamers is selected from Sgc8, TD05, sgc3b, Sgd5, KH2B05, KH1A02, KH1C12, TLS11a, PP3, TV02, HCH07, KDED2a-3, KCHA10, S11e, DOV4, aptTOV1, KMF2-1a, EJ2, CSC01, SYL3C, Anti-EGFR aptamer, or Anti-PSMA.

4. The device of claim 1, wherein said one or more aptamers and said one or more antibodies are capable of binding to the same biomolecules present on the surface of the target cell.

5. The device of claim 4, wherein said one or more aptamers and said one or more antibodies are capable of binding to Protein Tyrosine Kinase 7.

6. The device of claim 5, wherein the aptamer is sgc8 and the antibody is anti-PTK7 antibody.

7. The device of claim 1, wherein said one or more aptamers and said one or more antibodies are capable of binding to different biomolecules present on the surface of the target cell.

8. The device of claim 1, wherein said one or more aptamers and said one or more antibodies are attached to the inner surface of said one or more microfluidic channels in a non-covalent manner.

9. The device of claim 8, wherein said one or more aptamers and said one or more antibodies are attached to the inner surface of said one or more microfluidic channels via binding between one or more agents that are attached to said one or more aptamers and said one or more antibodies and one or more binding partners for the agents that are attached to the inner surface of said one or more microfluidic channels.

10. The device of claim 1, wherein said one or more aptamers and said one or more antibodies are attached to the inner surface of said one or more microfluidic channels by a spacer.

11. The device of claim 10, wherein the spacer is a cleavable spacer or an oligonucleotide (DNA) linker cleavable by an endonuclease.

12. The device of claim 10, wherein the spacer is a polymer.

13. The device of claim 1, wherein said device comprises an antibody that specifically binds to protein tyrosine kinase (PTK-7), epithelial cell adhesion molecule (EpCAM), E-cadherin, cytokeratin, zona occludens, laminin-1, entactin, syndecan, mucin-1, desmoplakin, collagen, CD-31, CD-34, CD-117, N-cadherin, vimentin, fibronectin, beta-catenin, integrin, Snail, Slug, forkhead box C2, epidermal growth factor receptor (EGFR), G-protein coupled receptors (GPCR) or prostate-specific membrane antigen (PSMA).

14. A method of isolating a target cell from a population of cells, the method comprising:
   a) passing the population of cells through the device of claim 1 under conditions that permit the interaction and capture of the target cell by said one or more aptamers and said one or more antibodies attached to the inner surface of the microfluidic channels,
   b) passing a wash buffer through said one or more microfluidic channels to remove the cells non-specifically bound to the aptamers and the antibodies,
   c) optionally, passing one or more reagents to verify that the captured cells are truly target cells,
   d) optionally, enumerating the cells captured,
   e) optionally, releasing the captured target cell from the scaffolding particle-ligand conjugates, and
   f) optionally collecting the released target cell.

15. The method of claim 14, wherein the population of cells originate from a tissue or body fluid of an organism.

16. The method of claim 15, wherein the tissue or body fluid is processed to prepare a sample containing the population of cells.

17. The method of claim 16, wherein the tissue is homogenized to prepare a slurry or solution containing the population of cells.

18. The method of claim 17, wherein the body fluid of the organism is blood from the organism.

19. The method of claim 18, wherein the blood is treated to lyse red blood cells found in said blood without damaging other cellular components found in said blood.

* * * * *

SEQUENCE LISTING

```
<160> NUMBER OF SEQ ID NOS: 22

<210> SEQ ID NO 1
<211> LENGTH: 41
<212> TYPE: DNA
<213> ORGANISM: Artificial Sequence
<220> FEATURE:
<223> OTHER INFORMATION: Sgc8 aptamer

<400> SEQUENCE: 1
atctaactgc tgcgccgccg ggaaaatact gtacggttag a              41

<210> SEQ ID NO 2
<211> LENGTH: 48
<212> TYPE: DNA
<213> ORGANISM: Artificial Sequence
```

```
<220> FEATURE:
<223> OTHER INFORMATION: TD05 aptamer

<400> SEQUENCE: 2
aacaccgtgg aggatagttc ggtggctgtt cagggtctcc tcccggtg                48

<210> SEQ ID NO 3
<211> LENGTH: 51
<212> TYPE: DNA
<213> ORGANISM: Artificial Sequence
<220> FEATURE:
<223> OTHER INFORMATION: sgc3b aptamer

<400> SEQUENCE: 3
acttattcaa ttcctgtggg aaggctatag aggggccagt ctatgaataa g            51

<210> SEQ ID NO 4
<211> LENGTH: 88
<212> TYPE: DNA
<213> ORGANISM: Artificial Sequence
<220> FEATURE:
<223> OTHER INFORMATION: Sgd5 aptamer

<400> SEQUENCE: 4
ataccagctt attcaattat cgtgggtcac agcagcggtt gtgaggaaga aaggcggata   60
acagataata agatagtaag tgcaatct                                     88

<210> SEQ ID NO 5
<211> LENGTH: 78
<212> TYPE: DNA
<213> ORGANISM: Artificial Sequence
<220> FEATURE:
<223> OTHER INFORMATION: KH2B05 aptamer

<400> SEQUENCE: 5
atccagagtg acgcagcaca cacaacctgc tcataaactt tactctgctc gaaccatctc   60
tggacacggt ggcttagt                                                78

<210> SEQ ID NO 6
<211> LENGTH: 80
<212> TYPE: DNA
<213> ORGANISM: Artificial Sequence
<220> FEATURE:
<223> OTHER INFORMATION: KH1A02 aptamer

<400> SEQUENCE: 6
atccagagtg acgcagcagg catagatgtg cagctccaag gagaagaagg agttctgtgt   60
attggacacg gtggcttagt                                              80

<210> SEQ ID NO 7
<211> LENGTH: 78
<212> TYPE: DNA
<213> ORGANISM: Artificial Sequence
<220> FEATURE:
<223> OTHER INFORMATION: KH1C12 aptamer

<400> SEQUENCE: 7
atccagagtg acgcagcatg ccctagttac tactactctt tttagcaaac gccctcgctt   60
tggacacggt ggcttagt                                                78
```

```
<210> SEQ ID NO 8
<211> LENGTH: 63
<212> TYPE: DNA
<213> ORGANISM: Artificial Sequence
<220> FEATURE:
<223> OTHER INFORMATION: TLS11a aptamer

<400> SEQUENCE: 8
acagcatccc catgtgaaca atcgcattgt gattgttacg gtttccgcct catggacgtg      60
ctg                                                                   63

<210> SEQ ID NO 9
<211> LENGTH: 76
<212> TYPE: DNA
<213> ORGANISM: Artificial Sequence
<220> FEATURE:
<223> OTHER INFORMATION: PP3 aptamer

<400> SEQUENCE: 9
atccagagtg acgcagcacg agccagacat ctcacacctg ttgcatatac attttgcatg      60
gacacggtgg cttagt                                                     76

<210> SEQ ID NO 10
<211> LENGTH: 62
<212> TYPE: DNA
<213> ORGANISM: Artificial Sequence
<220> FEATURE:
<223> OTHER INFORMATION: TV02 aptamer

<400> SEQUENCE: 10
atcgtctgct ccgtccaata cctgcatata cactttgcat gtggtttggt gtgaggtcgt      60
gc                                                                    62

<210> SEQ ID NO 11
<211> LENGTH: 71
<212> TYPE: DNA
<213> ORGANISM: Artificial Sequence
<220> FEATURE:
<223> OTHER INFORMATION: HCH07 aptamer

<400> SEQUENCE: 11
taccagtgcg atgctcaggc cgatgtcaac tttttctaac tcactggttt tgcctgacgc      60
attcggttga c                                                          71

<210> SEQ ID NO 12
<211> LENGTH: 59
<212> TYPE: DNA
<213> ORGANISM: Artificial Sequence
<220> FEATURE:
<223> OTHER INFORMATION: KDED2a-3 aptamer

<400> SEQUENCE: 12
tgcccgcgaa aactgctatt acgtgtgaga ggaaagatca cgcgggttcg tggacacgg       59

<210> SEQ ID NO 13
<211> LENGTH: 81
<212> TYPE: DNA
<213> ORGANISM: Artificial Sequence
<220> FEATURE:
<223> OTHER INFORMATION: KCHA10 aptamer
```

<400> SEQUENCE: 13
atccagagtg acgcagcagg ggaggcgaga gcgcacaata acgatggttg ggacccaact    60
gtttggacac ggtggcttag t                                              81

<210> SEQ ID NO 14
<211> LENGTH: 45
<212> TYPE: DNA
<213> ORGANISM: Artificial Sequence
<220> FEATURE:
<223> OTHER INFORMATION: S11e aptamer

<400> SEQUENCE: 14
atgcgaacag gtgggtgggt tgggtggatt gttcggcttc ttgat                    45

<210> SEQ ID NO 15
<211> LENGTH: 71
<212> TYPE: DNA
<213> ORGANISM: Artificial Sequence
<220> FEATURE:
<223> OTHER INFORMATION: DOV4 aptamer

<400> SEQUENCE: 15
actcaacgaa cgctgtggag ggcatcagat taggatctat aggttcggac atcgtgagga    60
ccaggagagc a                                                         71

<210> SEQ ID NO 16
<211> LENGTH: 79
<212> TYPE: DNA
<213> ORGANISM: Artificial Sequence
<220> FEATURE:
<223> OTHER INFORMATION: aptTOV1 aptamer

<400> SEQUENCE: 16
atccagagtg acgcagcaga tctgtgtagg atcgcagtgt agtggacatt tgatacgact    60
ggctcgacac ggtggctta                                                 79

<210> SEQ ID NO 17
<211> LENGTH: 76
<212> TYPE: DNA
<213> ORGANISM: Artificial Sequence
<220> FEATURE:
<223> OTHER INFORMATION: KMF2-1a aptamer

<400> SEQUENCE: 17
aggcggcagt gtcagagtga atagggatg tacaggtctg cacccactcg aggagtgact    60
gagcgacgaa gacccc                                                    76

<210> SEQ ID NO 18
<211> LENGTH: 41
<212> TYPE: DNA
<213> ORGANISM: Artificial Sequence
<220> FEATURE:
<223> OTHER INFORMATION: EJ2 aptamer

<400> SEQUENCE: 18
agtggtcgaa ctacacatcc ttgaactgcg gaattatcta c                        41

<210> SEQ ID NO 19
<211> LENGTH: 75
<212> TYPE: DNA
<213> ORGANISM: Artificial Sequence
<220> FEATURE:
<223> OTHER INFORMATION: CSC01 aptamer

```
<400> SEQUENCE: 19
accttggctg tcgtgttgta ggtggtttgc tgcggtgggc tcaagaagaa agcgcaaagt    60
cagtggtcag agcgt                                                   75

<210> SEQ ID NO 20
<211> LENGTH: 48
<212> TYPE: DNA
<213> ORGANISM: Artificial Sequence
<220> FEATURE:
<223> OTHER INFORMATION: Anti-EpCAM aptamer (SYL3C)

<400> SEQUENCE: 20
cactacagag gttgcgtctg tcccacgttg tcatgggggg ttggcctg               48

<210> SEQ ID NO 21
<211> LENGTH: 117
<212> TYPE: DNA
<213> ORGANISM: Artificial Sequence
<220> FEATURE:
<223> OTHER INFORMATION: Anti-EGFR aptamer

<400> SEQUENCE: 21
ggcgcuccga ccuuagucuc ugugccgcua uaaugcacgg auuuaaucgc cguagaaaag    60
caugucaaag ccggaaccgu guagcacagc agagaauuaa augcccgcca ugaccag      117

<210> SEQ ID NO 22
<211> LENGTH: 34
<212> TYPE: DNA
<213> ORGANISM: Artificial Sequence
<220> FEATURE:
<223> OTHER INFORMATION: Anti-PSMA aptamer

<400> SEQUENCE: 22
accaagaccu gacuucuaac uaagucuacg uucc                              34
```